(12) United States Patent
Case et al.

(10) Patent No.: US 7,637,937 B2
(45) Date of Patent: Dec. 29, 2009

(54) IMPLANTABLE MEDICAL DEVICE WITH OPTIMIZED SHAPE

(75) Inventors: Brian C. Case, Bloomington, IN (US); Jacob A. Flagle, Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 361 days.

(21) Appl. No.: 11/099,713

(22) Filed: Apr. 6, 2005

(65) Prior Publication Data

US 2005/0228472 A1 Oct. 13, 2005

Related U.S. Application Data

(60) Provisional application No. 60/561,013, filed on Apr. 8, 2004.

(51) Int. Cl.
*A61F 2/06* (2006.01)
(52) U.S. Cl. .................................................. 623/1.15
(58) Field of Classification Search ......... 623/1.15–1.2, 623/1.24, 1.11
See application file for complete search history.

(56) References Cited

U.S. PATENT DOCUMENTS

| | | | |
|---|---|---|---|
| 3,589,392 A | 6/1971 | Meyer | |
| 3,714,671 A | 2/1973 | Edwards et al. | |
| 3,755,823 A | 9/1973 | Hancock | |
| 3,903,548 A | 9/1975 | Nakib | |
| 4,106,129 A | 8/1978 | Carpentier et al. | |
| 4,178,638 A | 12/1979 | Meyer | |
| 4,218,782 A | 8/1980 | Rygg | |
| 4,222,126 A | 9/1980 | Boretos et al. | |
| 4,291,420 A | 9/1981 | Reul | |
| 4,297,749 A | 11/1981 | Davis et al. | |
| 4,339,831 A | 7/1982 | Johnson | |
| 4,343,048 A | 8/1982 | Ross et al. | |
| 4,470,157 A | 9/1984 | Love | |
| 4,488,318 A | 12/1984 | Kaster | |
| 4,580,568 A | 4/1986 | Gianturco | |
| 4,605,407 A | 8/1986 | Black et al. | |
| 4,643,732 A | 2/1987 | Pietsch et al. | |

(Continued)

FOREIGN PATENT DOCUMENTS

WO    WO 96/32077 A1    10/1996

OTHER PUBLICATIONS

Dynamics of the Vascular System, John K-J Li, Series on Bioengineering and Biomedical Engineering, 6.1.2 Structural Properties of Veins, p. 174.
Dynamics of the Vascular System, John K-J Li, Series on Bioengineering and Biomedical Engineering, 6.1.2 Structural Properties of Veins, p. 174 Year: 2004.

*Primary Examiner*—Todd E Manahan
*Assistant Examiner*—Eric Blatt
(74) *Attorney, Agent, or Firm*—Brinks Hofer Gilson & Lione

(57) ABSTRACT

Medical devices for implantation in a body vessel, and methods of using and making the same, are provided. Embodiments of the invention relate to medical devices comprising a frame having cross-section that can substantially conform to body vessel shapes that have elliptical or circular cross-sections, and dynamically respond to changes in the cross-section of a body vessel. Frames with directionally-dependent radial compressibility or expandability characteristics are also provided. Medical devices comprising a frame and one or more valve members adapted to regulate fluid flow in a body vessel, such as a vein, are also provided.

8 Claims, 8 Drawing Sheets

U.S. PATENT DOCUMENTS

| | | |
|---|---|---|
| 4,655,771 A | 4/1987 | Wallsten |
| 4,665,906 A | 5/1987 | Jervis |
| 4,692,164 A | 9/1987 | Dzemeshkevich et al. |
| 4,725,274 A | 2/1988 | Lane et al. |
| 4,728,328 A | 3/1988 | Hughes et al. |
| 4,731,074 A | 3/1988 | Rousseau et al. |
| 4,733,665 A | 3/1988 | Palmaz |
| 4,759,759 A | 7/1988 | Walker et al. |
| 4,778,461 A | 10/1988 | Pietsch et al. |
| 4,851,000 A | 7/1989 | Gupta |
| 4,863,467 A | 9/1989 | Bokros |
| 4,904,254 A | 2/1990 | Lane |
| 4,935,030 A | 6/1990 | Alonso |
| 5,032,128 A | 7/1991 | Alonso |
| 5,035,706 A | 7/1991 | Giantureo et al. |
| 5,064,435 A | 11/1991 | Porter |
| 5,104,402 A | 4/1992 | Melbin |
| 5,147,389 A | 9/1992 | Lane |
| 5,151,105 A | 9/1992 | Kwan-Gett |
| 5,163,951 A | 11/1992 | Pinchuk et al. |
| 5,211,649 A | 5/1993 | Kohler et al. |
| 5,358,518 A | 10/1994 | Camilli |
| 5,366,473 A | 11/1994 | Winston et al. |
| 5,370,685 A | 12/1994 | Stevens |
| 5,375,612 A | 12/1994 | Cottenceau et al. |
| 5,376,112 A | 12/1994 | Duran |
| 5,376,113 A | 12/1994 | Jansen et al. |
| 5,397,351 A | 3/1995 | Pavcnik et al. |
| 5,411,552 A | 5/1995 | Andersen et al. |
| 5,413,599 A | 5/1995 | Imachi et al. |
| 5,423,887 A | 6/1995 | Love et al. |
| 5,449,384 A | 9/1995 | Johnson |
| 5,469,868 A | 11/1995 | Reger |
| 5,476,471 A | 12/1995 | Shifrin et al. |
| 5,489,298 A | 2/1996 | Love et al. |
| 5,500,014 A | 3/1996 | Quijano et al. |
| 5,509,930 A | 4/1996 | Love |
| 5,545,214 A | 8/1996 | Stevens |
| 5,591,195 A | 1/1997 | Taheri et al. |
| 5,607,465 A | 3/1997 | Camilli |
| 5,607,471 A | 3/1997 | Seguin et al. |
| 5,609,598 A | 3/1997 | Laufer et al. |
| 5,609,626 A | 3/1997 | Quijano et al. |
| 5,683,448 A | 11/1997 | Cragg |
| 5,713,953 A | 2/1998 | Vallana et al. |
| 5,730,136 A | 3/1998 | Laufer et al. |
| 5,733,325 A | 3/1998 | Robinson et al. |
| 5,746,766 A | 5/1998 | Edoga |
| 5,755,782 A | 5/1998 | Love et al. |
| 5,769,780 A | 6/1998 | Hata et al. |
| 5,792,155 A | 8/1998 | Van Cleef et al. |
| 5,800,408 A | 9/1998 | Strauss et al. |
| 5,800,522 A | 9/1998 | Campbell et al. |
| 5,810,847 A | 9/1998 | Laufer et al. |
| 5,824,042 A | 10/1998 | Lombardi et al. |
| 5,824,043 A | 10/1998 | Cottone, Jr. |
| 5,824,054 A | 10/1998 | Khosravi et al. |
| 5,824,061 A | 10/1998 | Quijano et al. |
| 5,840,081 A | 11/1998 | Andersen et al. |
| 5,843,167 A | 12/1998 | Dwyer et al. |
| 5,843,171 A | 12/1998 | Campbell et al. |
| 5,851,232 A | 12/1998 | Lois |
| 5,855,597 A | 1/1999 | Jayaraman |
| 5,855,601 A | 1/1999 | Bessler et al. |
| 5,868,768 A | 2/1999 | Wicherski et al. |
| 5,879,382 A | 3/1999 | Boneau |
| 5,891,193 A | 4/1999 | Robinson et al. |
| 5,895,419 A | 4/1999 | Tweden et al. |
| 5,902,334 A | 5/1999 | Dwyer et al. |
| 5,925,063 A | 7/1999 | Khosravi |
| 5,935,161 A | 8/1999 | Robinson et al. |
| 5,954,766 A | 9/1999 | Zadno-Azizi et al. |
| 5,957,949 A | 9/1999 | Leonhardt et al. |
| 5,961,546 A | 10/1999 | Robinson et al. |
| 5,980,565 A | 11/1999 | Jayaraman |
| 5,997,573 A | 12/1999 | Quijano et al. |
| 6,004,347 A | 12/1999 | McNamara et al. |
| 6,015,431 A | 1/2000 | Thornton et al. |
| 6,022,374 A | 2/2000 | Imran |
| 6,033,398 A | 3/2000 | Farley et al. |
| 6,036,687 A | 3/2000 | Laufer et al. |
| 6,110,201 A | 8/2000 | Quijano et al. |
| 6,126,686 A | 10/2000 | Badylak et al. |
| 6,136,025 A | 10/2000 | Barbut et al. |
| 6,139,575 A | 10/2000 | Shu et al. |
| 6,143,022 A | 11/2000 | Shull et al. |
| 6,149,660 A | 11/2000 | Laufer et al. |
| 6,162,245 A | 12/2000 | Jayaraman |
| 6,168,614 B1 | 1/2001 | Andersen et al. |
| 6,176,875 B1 | 1/2001 | Lenker et al. |
| 6,187,036 B1 | 2/2001 | Shaolian et al. |
| 6,200,336 B1 | 3/2001 | Pavcnik et al. |
| 6,221,091 B1 | 4/2001 | Khosravi |
| 6,231,507 B1 | 5/2001 | Zikorus et al. |
| 6,241,763 B1 | 6/2001 | Drasler et al. |
| 6,245,102 B1 | 6/2001 | Jayaraman |
| 6,254,564 B1 | 7/2001 | Wilk et al. |
| 6,264,685 B1 * | 7/2001 | Ahari .................. 623/1.15 |
| 6,269,819 B1 | 8/2001 | Oz et al. |
| 6,280,467 B1 | 8/2001 | Leonhardt |
| 6,287,334 B1 | 9/2001 | Moll et al. |
| 6,287,335 B1 | 9/2001 | Drasler et al. |
| 6,287,339 B1 | 9/2001 | Vazquez et al. |
| 6,290,721 B1 | 9/2001 | Heath |
| 6,293,968 B1 | 9/2001 | Taheri |
| 6,296,661 B1 | 10/2001 | Davila et al. |
| 6,299,636 B1 | 10/2001 | Schmitt et al. |
| 6,299,637 B1 | 10/2001 | Shaolian et al. |
| 6,315,791 B1 | 11/2001 | Gingras et al. |
| 6,315,793 B1 | 11/2001 | Bokros et al. |
| 6,334,868 B1 | 1/2002 | Ham |
| 6,334,873 B1 | 1/2002 | Lane et al. |
| 6,342,070 B1 | 1/2002 | Nguyen-Thien-Nhon et al. |
| 6,344,052 B1 | 2/2002 | Greenan et al. |
| 6,361,496 B1 | 3/2002 | Zikorus et al. |
| 6,425,916 B1 | 7/2002 | Garrison et al. |
| 6,440,164 B1 | 8/2002 | DiMatteo et al. |
| 6,451,051 B2 | 9/2002 | Drasler et al. |
| 6,454,799 B1 | 9/2002 | Schreck |
| 6,458,153 B1 | 10/2002 | Bailey et al. |
| 6,478,819 B2 | 11/2002 | Moe |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,527,800 B1 | 3/2003 | McGuckin, Jr. et al. |
| 6,562,068 B2 | 5/2003 | Drasler et al. |
| 6,562,069 B2 | 5/2003 | Cai et al. |
| 6,575,971 B2 | 6/2003 | Hauck et al. |
| 6,582,462 B1 | 6/2003 | Andersen et al. |
| 6,585,761 B2 | 7/2003 | Taheri |
| 6,602,286 B1 | 8/2003 | Strecker |
| 6,605,112 B1 | 8/2003 | Moll et al. |
| 6,632,243 B1 | 10/2003 | Zadno-Azizi et al. |
| 6,652,578 B2 | 11/2003 | Bailey et al. |
| 6,666,886 B1 | 12/2003 | Tranquillo et al. |
| 6,676,698 B2 | 1/2004 | McGuckin, Jr. et al. |
| 6,685,739 B2 | 2/2004 | DiMatteo et al. |
| 6,689,161 B2 | 2/2004 | Chen et al. |
| 6,695,833 B1 | 2/2004 | Frantzen |
| 6,695,878 B2 | 2/2004 | McGuckin, Jr. et al. |
| 6,705,585 B1 | 3/2004 | Roy |
| 6,716,241 B2 | 4/2004 | Wilder et al. |
| 6,730,118 B2 | 5/2004 | Spenser et al. |
| 6,752,828 B2 | 6/2004 | Thornton |

| | | | | | | |
|---|---|---|---|---|---|---|
| 6,764,510 B2 | 7/2004 | Vidlund et al. | | 2003/0195618 A1 | 10/2003 | Abraham et al. |
| 6,830,585 B1 | 12/2004 | Artof et al. | | 2003/0199971 A1 | 10/2003 | Tower et al. |
| 6,840,957 B2 | 1/2005 | DiMatteo et al. | | 2003/0199972 A1 | 10/2003 | Zadno-Azizi et al. |
| 6,875,231 B2 | 4/2005 | Anduiza et al. | | 2003/0208261 A1 | 11/2003 | Thorpe et al. |
| 7,273,492 B2 | 9/2007 | Cheng et al. ............... 632/1.11 | | 2003/0209835 A1* | 11/2003 | Chun et al. ................ 264/339 |
| 7,279,003 B2 | 10/2007 | Berra et al. ................ 623/1.13 | | 2003/0212452 A1 | 11/2003 | Zadno-Azizi et al. |
| 2001/0005787 A1 | 6/2001 | Oz et al. | | 2003/0216764 A1 | 11/2003 | Tu et al. |
| 2001/0007956 A1 | 7/2001 | Letac et al. | | 2003/0225447 A1 | 12/2003 | Majercak et al. |
| 2001/0010017 A1 | 7/2001 | Letac et al. | | 2003/0229393 A1 | 12/2003 | Kutryk et al. |
| 2001/0011187 A1 | 8/2001 | Pavcnik et al. | | 2003/0236568 A1 | 12/2003 | Hojeibane et al. |
| 2001/0011189 A1 | 8/2001 | Drasler et al. | | 2004/0002719 A1 | 1/2004 | Oz et al. |
| 2001/0021872 A1 | 9/2001 | Bailey et al. | | 2004/0015230 A1 | 1/2004 | Moll et al. |
| 2001/0039450 A1 | 11/2001 | Pavcnik et al. | | 2004/0019374 A1 | 1/2004 | Hojeibane et al. |
| 2001/0044654 A1 | 11/2001 | Chen et al. | | 2004/0024445 A1* | 2/2004 | Dickson .................... 623/1.19 |
| 2001/0047198 A1 | 11/2001 | Drasler et al. | | 2004/0024447 A1 | 2/2004 | Haverich |
| 2002/0002401 A1 | 1/2002 | McGuckin et al. | | 2004/0024452 A1 | 2/2004 | Kruse et al. |
| 2002/0032481 A1* | 3/2002 | Gabbay .................... 623/2.11 | | 2004/0034408 A1 | 2/2004 | Majercak et al. |
| 2002/0055772 A1 | 5/2002 | McGuckin et al. | | 2004/0039436 A1 | 2/2004 | Spenser et al. |
| 2002/0077696 A1 | 6/2002 | Zadno-Azizi et al. | | 2004/0044393 A1* | 3/2004 | Yarden et al. .............. 623/1.2 |
| 2002/0095209 A1 | 7/2002 | Zadno-Azizi et al. | | 2004/0049266 A1 | 3/2004 | Anduiza et al. |
| 2002/0099439 A1 | 7/2002 | Schwartz et al. | | 2004/0054396 A1 | 3/2004 | Hartley et al. |
| 2002/0107565 A1* | 8/2002 | Greenhalgh ............... 623/1.24 | | 2004/0059411 A1 | 3/2004 | Strecker |
| 2002/0123800 A1 | 9/2002 | Taheri | | 2004/0092858 A1 | 5/2004 | Wilson et al. |
| 2002/0138135 A1 | 9/2002 | Duerig et al. | | 2004/0093070 A1 | 5/2004 | Hojeibane et al. |
| 2002/0151970 A1 | 10/2002 | Garrison et al. | | 2004/0098098 A1 | 5/2004 | McGuckin et al. |
| 2002/0177894 A1 | 11/2002 | Acosta et al. | | 2004/0098112 A1 | 5/2004 | DiMatteo et al. |
| 2002/0188348 A1 | 12/2002 | DiMatteo et al. | | 2004/0106976 A1 | 6/2004 | Bailey et al. |
| 2003/0018358 A1 | 1/2003 | Saadat | | 2004/0137618 A1 | 7/2004 | Chen et al. |
| 2003/0023300 A1 | 1/2003 | Bailey et al. | | 2004/0138684 A1 | 7/2004 | Eton |
| 2003/0023303 A1 | 1/2003 | Palmaz et al. | | 2004/0167619 A1 | 8/2004 | Case et al. |
| 2003/0036795 A1 | 2/2003 | Andersen et al. | | 2004/0186558 A1 | 9/2004 | Pavcnik et al. |
| 2003/0040792 A1 | 2/2003 | Gabbay | | 2004/0193253 A1 | 9/2004 | Thorpe et al. |
| 2003/0055492 A1 | 3/2003 | Shaolian et al. | | 2004/0199183 A1 | 10/2004 | Oz et al. |
| 2003/0055495 A1 | 3/2003 | Pease et al. | | 2004/0210301 A1 | 10/2004 | Obermiller |
| 2003/0055496 A1 | 3/2003 | Cai et al. | | 2004/0210306 A1 | 10/2004 | Quijano et al. |
| 2003/0060875 A1 | 3/2003 | Wittens | | 2004/0210307 A1 | 10/2004 | Khairkhahan |
| 2003/0083741 A1 | 5/2003 | Woo et al. | | 2004/0215339 A1 | 10/2004 | Drasler et al. |
| 2003/0093071 A1 | 5/2003 | Hauck et al. | | 2004/0225352 A1 | 11/2004 | Osborne et al. |
| 2003/0114913 A1 | 6/2003 | Spenser et al. | | 2004/0243222 A1 | 12/2004 | Osborne et al. |
| 2003/0125795 A1 | 7/2003 | Pavcnik et al. | | 2004/0254636 A1 | 12/2004 | Flagle et al. |
| 2003/0130726 A1 | 7/2003 | Thorpe et al. | | 2004/0260389 A1 | 12/2004 | Case et al. |
| 2003/0130727 A1 | 7/2003 | Drasler et al. | | 2004/0260390 A1 | 12/2004 | Sarac et al. |
| 2003/0149477 A1 | 8/2003 | Gabbay | | 2005/0027348 A1 | 2/2005 | Case et al. |
| 2003/0171802 A1 | 9/2003 | Wilder et al. | | 2005/0049692 A1 | 3/2005 | Numamoto et al. |
| 2003/0171824 A1 | 9/2003 | Abraham et al. | | 2005/0065594 A1 | 3/2005 | DiMatteo et al. |
| 2003/0181974 A1* | 9/2003 | Xie et al. ................... 623/1.24 | | 2005/0075728 A1* | 4/2005 | Nguyen et al. ............. 623/2.17 |
| 2003/0191525 A1 | 10/2003 | Thornton | | 2007/0185560 A1 | 8/2007 | Roeder et al. .............. 623/1.15 |
| 2003/0191528 A1 | 10/2003 | Quijano et al. | | * cited by examiner | | |

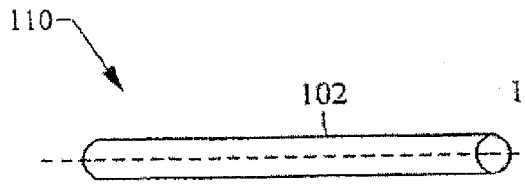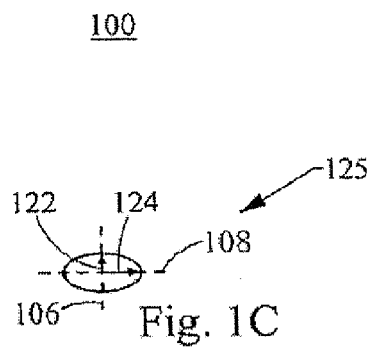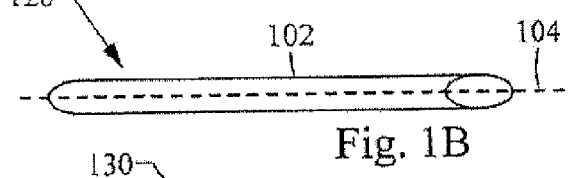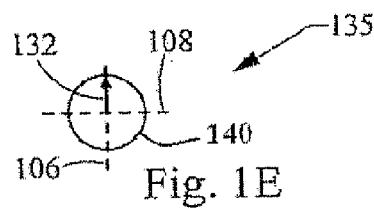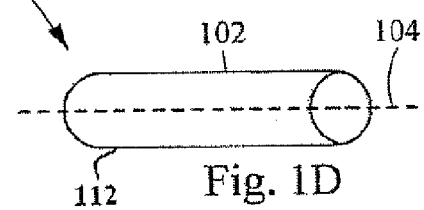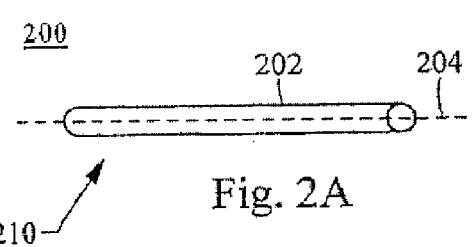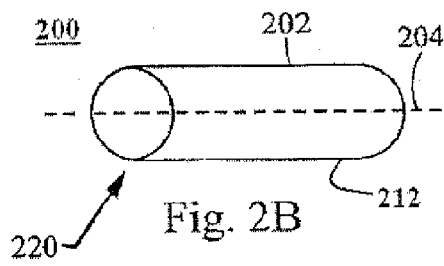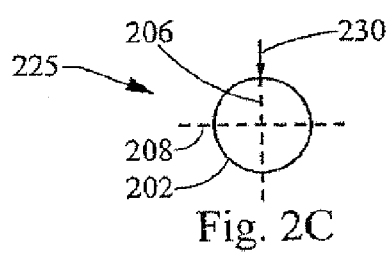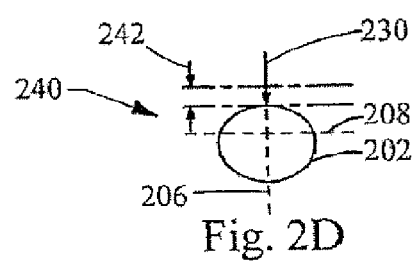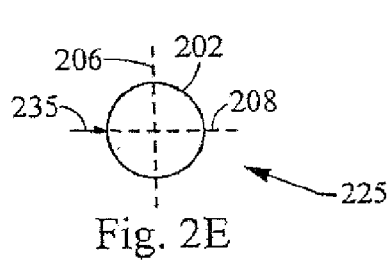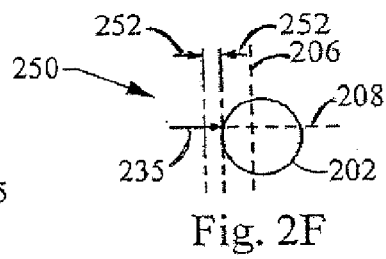

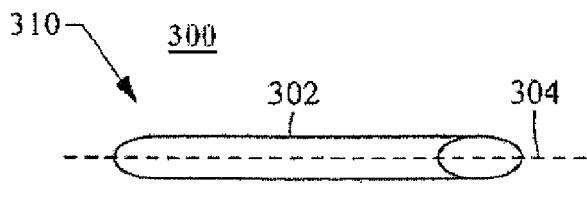
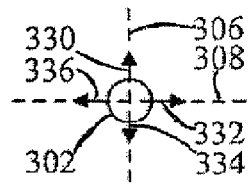
Fig. 3A Fig. 3B
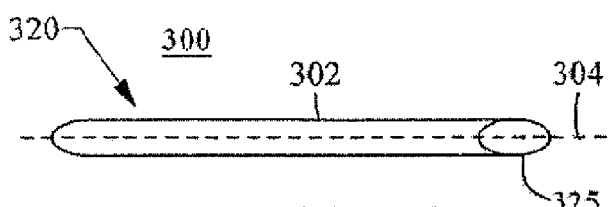
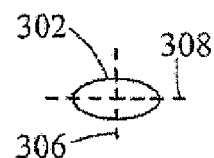
Fig. 3C Fig. 3D
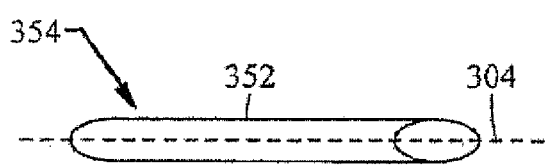
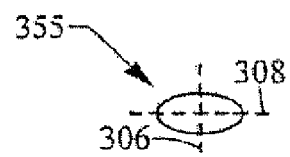
Fig. 4A Fig. 4B
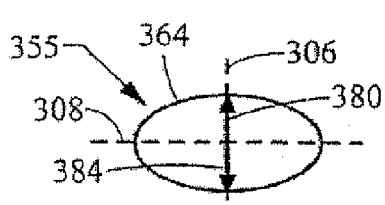
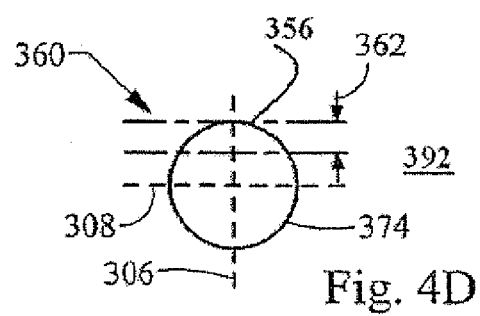
Fig. 4C Fig. 4D
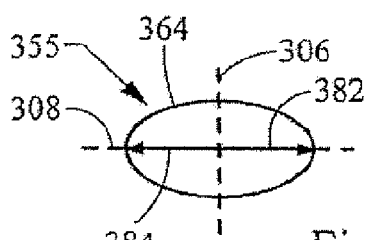
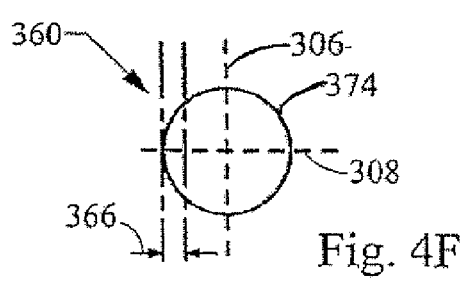
Fig. 4E Fig. 4F

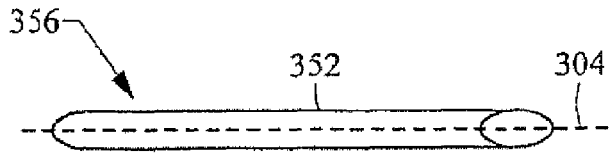
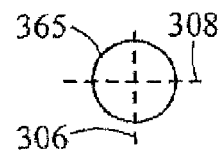
Fig. 4G    Fig. 4H
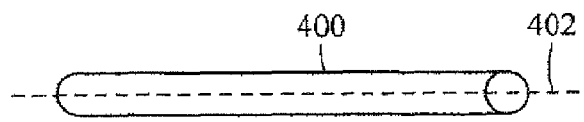
Fig. 5A
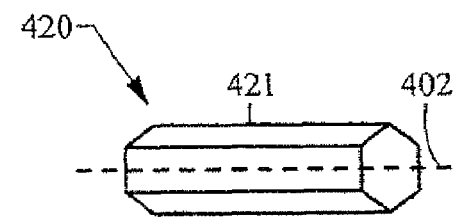
Fig. 5B
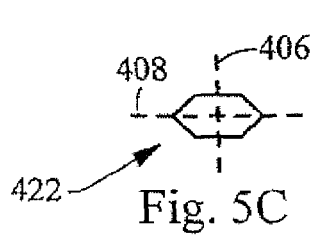 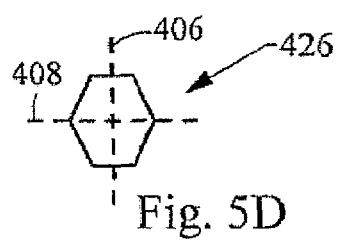
Fig. 5C    Fig. 5D
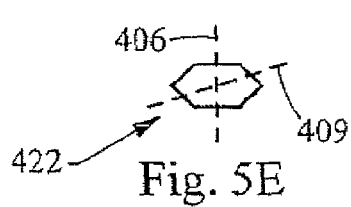 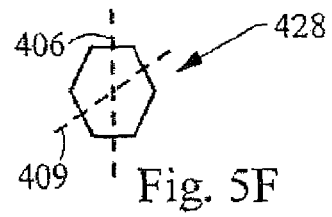
Fig. 5E    Fig. 5F

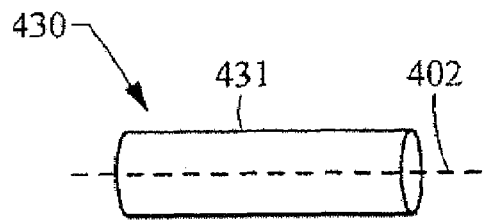
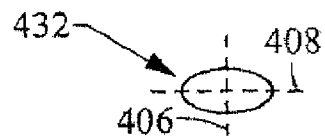
Fig. 5G  Fig. 5H
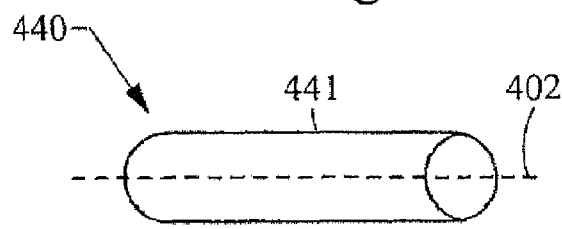
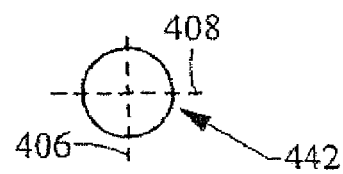
Fig. 5I  Fig. 5J
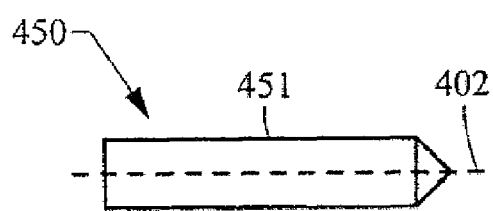
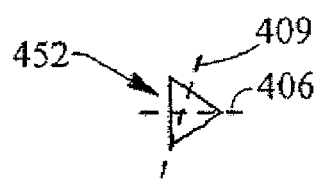
Fig. 5K  Fig. 5L
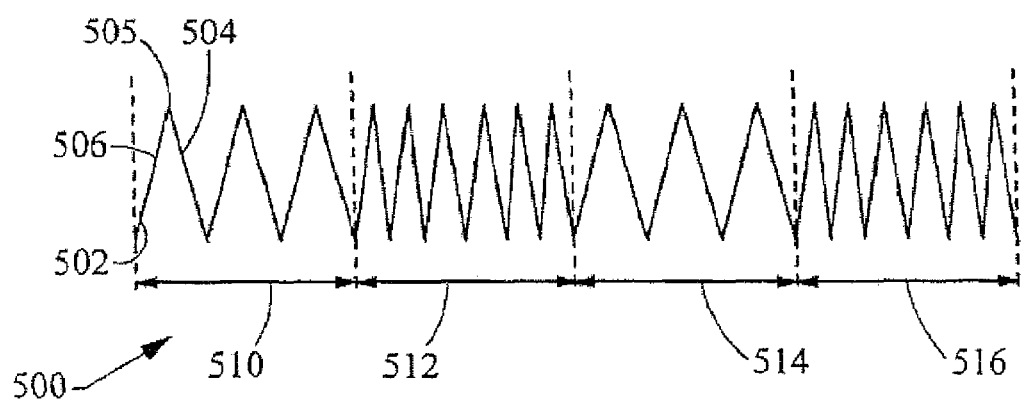
Fig. 6A

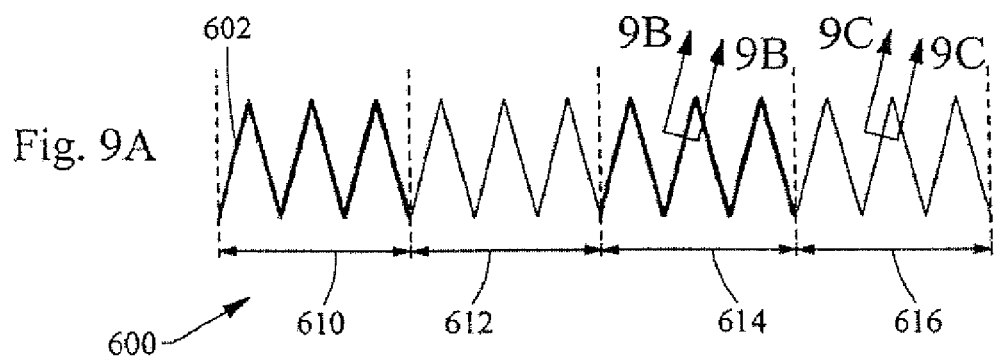
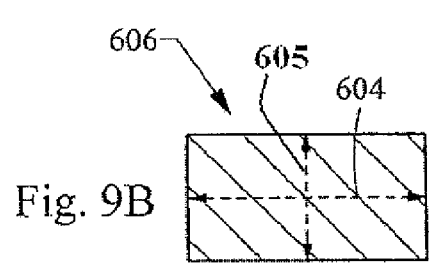
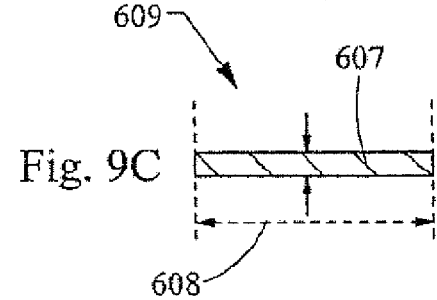
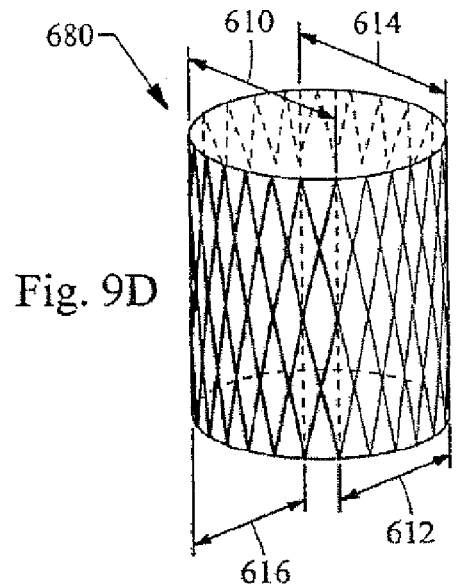
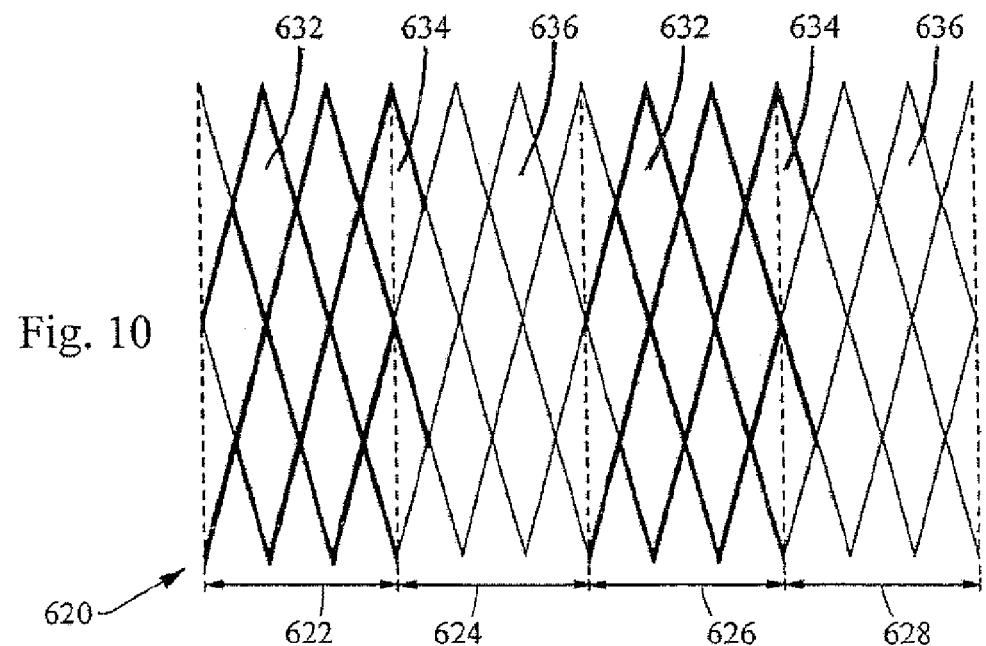

IMPLANTABLE MEDICAL DEVICE WITH OPTIMIZED SHAPE

RELATED APPLICATIONS

This application claims priority to U.S. Provisional Patent Application Ser. No. 60/561,013, filed Apr. 8, 2004, and entitled, "Implantable Medical Device with Optimized Shape," which is incorporated by reference herein in its entirety.

TECHNICAL FIELD

The present invention relates to medical devices. More particularly, the invention relates to medical devices for implantation in a body vessel.

BACKGROUND

Many vessels in animals transport fluids from one body location to another. Frequently, fluid flows in a substantially unidirectional manner along the length of the vessel. For example, veins in the body transport blood to the heart and arteries carry blood away from the heart.

Recently, various implantable medical devices and minimally invasive methods for implantation of these devices have been developed to deliver these medical devices within the lumen of a body vessel. These devices are advantageously inserted intravascularly, for example from an implantation catheter. For example, implantable medical devices can function as a replacement venous valve, or restore native venous valve function by bringing incompetent valve leaflets into closer proximity. Such devices can comprise an expandable frame configured for implantation in the lumen of a body vessel, such as a vein. Venous valve devices can further comprise features that provide a valve function, such as opposable leaflets.

Dynamic fluctuations in the shape of the lumen of a vein pose challenges to the design of implantable prosthetic devices that conform to the interior shape of the lumen of a vein. Unlike arterial vessels, the flow velocity and diameter of veins does not remain essentially constant at a given systemic vascular resistance. Instead, the shape of vein lumens can fluctuate dynamically in response to the respiration, body position, central venous pressure, arterial inflow and calf muscle pump action of a mammalian subject. The veins also provide the principal volume capacitance organ. For example, an increase of almost 100% in the diameter of the common femoral vein has been observed in human patients simply by rotation of the patient by about 40 degrees, corresponding to a four-fold increase in blood flow volume. Moneta et al., "Duplex untrasound assessment of venous diameters, peak velocities and flow patterns," J. Vasc. Surg. 1988; 8; 286-291. Therefore, the shape of a lumen of a vein, which is substantially elliptical in cross-section, can undergo dramatic dynamic change as a result of varying blood flow velocities and volumes therethrough, presenting challenges for designing implantable intraluminal prosthetic devices that more closely conform to the changing shape of the vein lumen.

Implantable devices for treating venous valve insufficiency are often not designed to be responsive to dynamic changes in the shape of a body vessel lumen, such as in a vein. Implantable prosthetic stents or valves for veins often have the same compressibility or expandability in any radial direction. Similarly, implantable device configurations can be unresponsive to dynamic changes of the vessel cross-section, and can locally distort the shape of the body vessel.

There exists a need in the art for an implantable prosthetic device frame that is capable of better conforming to the shape of the vessel lumen, and being more responsive to dynamic changes in body vessel lumen shape. There is a further need for an intraluminal prosthetic device comprising an expandable frame or valve that can be deployed in vessels to replace or augment incompetent native valves, such that the frame or valve provides improved conformation to the shape of vein lumens and dynamic changes thereof. Such a device can closely simulate the normal vessel shape and responsiveness, as well as normal valve function, while being capable of permanent implantation with excellent biocompatibility.

SUMMARY

The invention relates to medical devices for implantation in a body vessel. More specifically, preferred embodiments relate to a medical device comprising a frame having a cross-section that can substantially conform to body vessel shapes that have elliptical or circular cross-sections, and can change shape in response to changes in the cross-section of a body vessel.

In one embodiment, a frame can expand from a compressed, or unexpanded, delivery configuration to one or more radially expanded deployment configurations, for example through self-expansion or balloon expansion of the frame. The expanded configuration can have any suitable cross-sectional configuration, including circular or elliptical. In one embodiment, the frame can be oriented along the longitudinal axis of a body vessel in the expanded or compressed configurations. In certain embodiments, the frame in its expanded or compressed configurations can be moveable from or to a configuration having a circular cross-section and a configuration having an elliptical cross-section. In one embodiment, the expanded configuration is itself readily moveable between a circular tubular configuration and elliptical tubular configuration, for example in response to conformational changes in the interior wall of a vein or other body vessel.

The frame, in one embodiment, is characterized by a first radial compressibility along a first radial direction that is less than a second radial compressibility along a second direction. The frame can also, in some embodiments, be characterized by a first radial expandability along a first radial direction that is less than a second radial expandability along a second direction. In other embodiments, during expansion, a frame can exert a first radial expansion force along a first radial direction and a second, lesser, expansion force along a second radial direction.

Radial directions can be oriented in any suitable absolute orientation with respect to a body vessel. Where indicated, relationships of multiple radial directions with respect to each other are provided. For example, in some embodiments, the first and second radial directions are perpendicular to the longitudinal axis of the body vessel and in a cross-sectional plane of the frame. The first and second radial directions may also be perpendicular to each other in certain embodiments. However, the first and second radial directions can also be oriented at less than or greater than 90-degrees with respect to each other within the cross-sectional plane of the frame.

In some embodiments, the frame in the expanded configuration, the compressed configuration, or both, have a first maximum radial distance that is greater than a second maximum radial distance. For instance, in one embodiment, the frame has an elliptical cross-section. In other embodiments, the frame comprises a continuous, circular cross-section at one or more portions of the frame while in an expanded or compressed configuration.

The frame can, in one embodiment, comprise a plurality of struts, which can be of any suitable structure or orientation to allow the frame to provide a particular compressibility, expandability, radial expansion force, or any combination thereof. In one embodiment, the frame comprises a plurality of struts connected by alternating bends. For example, the frame can be an annular ring member comprising a series of struts in a "zig-zag" pattern. The frame can also comprise multiple annular ring members with struts in a "zig-zag" pattern, for example by connecting the annular ring members end to end, or in an overlapping fashion. In some embodiments, the struts are substantially aligned along the surface of a tubular plane, substantially parallel to the longitudinal axis of the support frame. The frame can, in some embodiments, have a non-uniform density of struts. For example, the frame can comprise a first circumferential region having continuously joined regions of a first and a second strut density per unit of circumferential distance which intersect the first and second radial directions, respectively. In one embodiment, the first strut density is greater than the second strut density. In other embodiments, the frame struts can have non-uniform cross-sectional areas. For instance, portions of a strut can have a first cross-sectional area that is less than a second cross-sectional area of another portion of the same strut or a portion of a different strut.

Also provided are embodiments wherein the frame comprises a means for orienting the frame within a body lumen. For example, the frame can comprise a marker, or a delivery device comprising the frame can provide indicia relating to the orientation of the frame within the body vessel.

The invention also relates to embodiments comprising a frame and a means for regulating fluid through a body vessel. In some embodiments, the fluid can flow through the frame, while other embodiments provide for fluid flow through a lumen defined by the frame. In some embodiments, the frame can be a tubular structure that defines a lumen having a circular or elliptical cross section, or a frame that is moveable between a configuration defining a lumen with a circular cross section and a lumen with an elliptical cross section. Some embodiments comprise a frame and a first valve member connected to the frame. A valve member, according to some embodiments, can comprise a leaflet comprising a free edge, responsive to the flow of fluid through the body vessel. For example, one or more valve members attached to a frame may, in one embodiment, permit fluid to flow through a body vessel in a first direction while substantially preventing fluid flow in the opposite direction. In some embodiments, the valve member comprises an extracellular matrix material, such as small intestine submucosa (SIS).

Other embodiments provide methods of making medical devices described herein. Still other embodiments provide methods of treating a subject, which can be animal or human, comprising the step of implanting one or more support frames as described herein. Other methods further comprise the step of implanting one or more frames attached to one or more valve members, as described herein. In some embodiments, methods of treating may also include the step of delivering a medical device to a point of treatment in a body vessel, or deploying a medical device at the point of treatment, wherein the medical devices are as described herein. Methods for treating certain conditions are also provided, such as venous valve insufficiency, varicose veins, esophageal reflux, restinosis or atherosclerosis. Methods for delivering a medical device as described herein to any suitable body vessel are also provided, such as a vein, artery, billiary duct, ureteral vessel, body passage or portion of the alimentary canal.

The invention includes other embodiments within the scope of the claims, and variations of all embodiments, and is limited only by the claims made by the Applicants. Additional understanding of the invention can be obtained by referencing the detailed description of embodiments of the invention, below, and the appended drawings.

BRIEF DESCRIPTION OF THE DRAWINGS

FIG. 1A is a perspective view of a medical device in a compressed delivery configuration; FIG. 1B is a perspective view and FIG. 1C is a corresponding end view of the medical device of FIG. 1A in an elliptical expanded configuration; and FIG. 1D is a perspective view and FIG. 1E is a corresponding end view of the medical device of FIG. 1A in a circular expanded configuration.

FIG. 2A is a perspective view of a medical device in a compressed delivery configuration; FIG. 2B is a perspective view of the medical device of FIG. 2A in a circular expanded configuration. FIGD. 2C and 2D are end views of the medical device of FIG. 2B showing the radial compressibility of the medical device to a force along a first direction. FIGS. 2E and 2F are end views of the medical device of FIG. 2B showing the radial compressibility of the medical device to a force along a second direction.

FIG. 3A shows a perspective view, with a corresponding end view in FIG. 3B, of a medical device in a compressed configuration having a circular cross-section. FIG. 3C shows the same medical device in an expanded configuration, having an elliptical cross-section, shown in the corresponding end view of FIG. 3D.

FIG. 4A is a perspective view of a medical device in a compressed delivery configuration, with a corresponding end view shown in FIG. 4B; FIG. 4G is a perspective view of the medical device of FIG. 4A in a circular expanded configuration, with a corresponding end view shown in FIG. 4H. FIGS. 4C and 4D are all end views of the medical device of FIG. 4G showing the radial compressibility of the medical device to a force along a first direction or a second direction. FIGS. 4E and 4F are end views of the medical device of FIG. 4G showing the radial compressibility of the medical device to a force along a second direction.

FIG. 5A is a perspective view of a medical device in a compressed delivery configuration with a circular cross section. FIG. 5B is a perspective view of a medical device in an expanded configuration having a hexagonal cross section, and optionally characterized by differing expandability or compressibility along different directions, as illustrated in the end views of FIGS. 5C, 5D, 5E and 5F, all of which correspond to the expanded frame of FIG. 5B. FIG. 5G is a perspective view of a medical device in an expanded configuration having an oval cross section, as shown in the corresponding end view of FIG. 5H. FIG. 5I is a perspective view of a medical device in an expanded configuration having a circular cross section, as shown in the corresponding end view of FIG. 5J. FIG. 5K is a perspective view of a medical device in an expanded configuration having an triangular cross section, as shown in the corresponding end view of FIG. 5L.

FIG. 9A is a diagram of an expandable medical device frame having various strut cross-sectional areas, shown in strut cross sectional views of FIGS. 9B and 9C. FIG. 9D shows the tubular configuration of the medical device frame of FIG. 9A.

FIG. 10 is a diagram of an expandable medical device frame having various strut cross-sectional areas.

DETAILED DESCRIPTION OF EMBODIMENTS

Figure 6B:
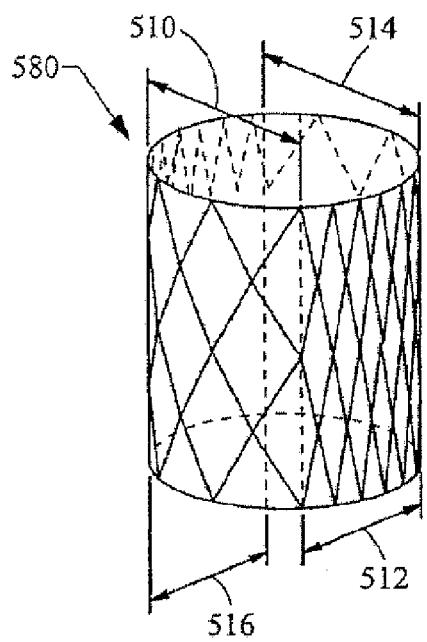
FIG. 6B shows an end view of the medical device frame of FIG. 6A in a circular tubular configuration that is moveable to a second elliptical tubular configuration shown in the end view of FIG. 6C.

The following detailed description and appended drawings describe and illustrate various exemplary embodiments of the invention. The description and drawings serve to enable one skilled in the art to make and use the invention, and are not intended to limit the scope of the invention in any manner.

The invention provides medical devices for implantation in a body vessel, methods of making the medical devices, and methods of treatment that utilize the medical devices.

As used herein, the term "implantable" refers to an ability of a medical device to be positioned at a location within a body, such as within a body vessel. Furthermore, the terms "implantation" and "implanted" refer to the positioning of a medical device at a location within a body, such as within a body vessel.

The invention relates to medical devices for implantation in a body vessel. More specifically, embodiments of the invention relate to a medical device comprising a frame having a cross-section that can substantially conform to body vessel shapes that have elliptical or circular cross-sections, and dynamically respond to changes in the cross-section of a body vessel.

In one embodiment, a frame can expand from a compressed, or unexpanded, delivery configuration to one or more radially expanded deployment configurations, for example through self-expansion or balloon expansion of the frame. The expanded configuration can have any suitable cross-sectional configuration, including circular or elliptical. In one embodiment, the frame can be oriented along the longitudinal axis of a body vessel in the expanded or compressed configurations. In one embodiment, the frame is moveable from a circular configuration having a circular cross-section and an elliptical configuration having an elliptical cross-section, which can be compressed or expanded configurations. In one embodiment, the expanded configuration is itself dynamically moveable between a circular tubular configuration and elliptical tubular configuration.

"Dynamic movement" refers to movement of the frame in response to external forces, such as changes in the dimensions of the lumen of a body vessel.

In preferred embodiments, when the frame changes shape, a radial compressibility, radial expandability or radial expansion force depend on the direction along which the frame is changing shape. For instance, a medical device comprises a frame that can be deflected more easily along one radial direction than another. Particularly preferred embodiments provide medical devices comprising a frame responsive to dynamic movement by the interior of a body vessel. For example, in one embodiment, a medical device comprises a frame that readily changes from an elliptical to a circular cross-section in response to corresponding changes in the cross-section of a body vessel lumen.

Also provided are medical devices comprising a frame of any suitable shape and configuration that possess particular expandability or compressibility characteristics set forth in various embodiments. The frame can be expandable or non-expandable, and be formed from any suitable materials.

The recitation of radial directions as "first," "second," and the like are provided merely for illustrative purposes without providing any required orientation of particular radial directions unless expressly stated (such as reciting "a first radial direction perpendicular to a second orientation," and the like). In some embodiments, a "first" radial direction can be perpendicular to a "second" radial direction and perpendicular to a longitudinal axis of a body vessel or a longitudinal axis of a frame. In other embodiments, a first and a second radial direction can be less than or greater than 90-degrees relative to each other, or with respect to a longitudinal axis of a body vessel or frame.

FIG. 1A is a perspective view of a medical device 100 according to a first embodiment of the invention. The medical device comprises a frame with a tubular frame body 102. The medical device 100 shown in a perspective view in FIG. 1B and an end view in FIG. 1C. The medical device 100 is delivered to a body vessel in a compressed configuration 110 substantially aligned with the longitudinal axis 104 of the body vessel (body vessel not shown), and is then expanded 112 to a radially-expanded configuration upon deployment within the body vessel. The tubular frame body 102 can be expanded by any suitable method, including self-expansion of the frame material or balloon expansion. Two expanded configurations are shown. The first expanded configuration 120, shown in the perspective view of FIG. 1B and the corresponding end view of FIG. 1C, has an elliptical cross-section 125. A second expanded configuration 130, shown in the perspective view of FIG. 1D and the corresponding end view of FIG. 1E, has a circular cross-section 135. The tubular body 102 is moveable 140 between the first expanded configuration 120 and the second configuration 130 in response to similar changes in the cross-section of the body vessel. The elliptical cross-section 125 of the first expanded configuration 120 has a first maximum radial distance 122 that is less than, and perpendicular to, a second maximum radial distance 124. In contrast, the circular cross-section 135 of the second expanded configuration 130 has a maximum radial distance 132 that is a radius that is constant around the circumference of the tubular body 102. The first maximum radial distance 122 can be oriented along a first radial direction 106 and the second maximum radial distance 124 can be oriented along a second radial direction 108.

In some embodiments, the first and second radial directions are perpendicular to the longitudinal axis of the body vessel and in a cross-sectional plane of the frame. The first and second radial directions can be perpendicular to each other in one embodiment. However, the first and second radial directions can also be oriented at less than or greater than 90 degrees with respect to each other within the cross-sectional plane of the frame. In the embodiments shown in FIGS. 1A-1E, the first radial direction 106 and the second radial direction 108 are perpendicular to the longitudinal axis 104 of the body vessel, in a cross-sectional plane of a body vessel.

The frame can also, in a second embodiment, be characterized by a first radial compressibility along a first radial direction that is less than a second radial compressibility along a second direction.

"Radial compressibility" refers to the radial displacement of the body frame in response to a given force directed radially inward toward the center of the frame. FIG. 2A is a perspective view of a medical device 200 in a compressed delivery configuration and FIG. 2B is a perspective view of the medical device 200 in an expanded configuration 220. The expanded configuration 220 has a first radial compressibility first direction, as shown in end views of FIGS. 2C and 2D, and a second radial compressibility in a second direction, as shown in end views of FIGS. 2E and 2F. The medical device 200 comprises a frame with a tubular frame body 202 having a compressed configuration 210 for intraluminal delivery to a body vessel. Upon radial expansion 212 within the body vessel, the tubular frame body 202 assumes an expanded configuration 220. The expanded configuration 220 has a circular cross-section 225 having at least two direction-specific radial compressibilities.

Radial compressibility is measured by comparing the radial frame displacement in response to a force applied radially inward to the frame along two different radial directions. The greater the displacement of the frame in response to the applied force in a particular direction, the greater the compressibility of the frame in that direction. The first radial compressibility is shown schematically in FIGS. 2C-2F. Referring to the end views of FIGS. 2C and 2D, a first force 230 is applied radially inward to the tubular frame body 202 along a first radial direction 206 (FIG. 2C), resulting in a first displacement 242 of the tubular frame body 202 (FIG. 2D). The second radial compressibility is shown schematically by the end views of FIGS. 2E and 2F. When a second force 235 of the same magnitude is applied radially inward to the tubular frame body 202 along a second radial direction 208 (FIG. 2E), a second displacement 252 of the tubular frame body 202 occurs (FIG. 2F). The first displacement 242 is greater than the second displacement 252, indicating that the frame is more compliant, or less stiff, along the first radial direction 206 than along the second radial direction 208. Therefore, the tubular body frame 202 has a first compressibility that is greater than the second compressibility.

In this embodiment, the first radial direction 206 is perpendicular to the second radial direction 208, and both of these directions are perpendicular to the longitudinal axis 204 of the tubular frame body 202. However, other configurations are also within the scope of the invention. For instance, other embodiments may provide two or more radial directions that are not perpendicular to each other or to the longitudinal axis of either the frame or the body vessel.

The frame can also, in a third embodiment, be characterized by a first radial expandability along a first radial direction that is less than a second radial expandability along a second direction.

"Radial expandability" refers to how easily a given force applied outward from inside the frame can displace the frame outward. The radial expandability can be same or different from the radial compressibility for a given frame embodiment. Radial expandability can be measured by comparing the radial frame displacement in response to a force applied to the frame radially outward, away from the center of the frame, along at least two different directions. Like measuring radial compressibility, the greater the displacement of the frame in response to the applied force in a particular direction, the greater the radial expandability of the frame in that direction.

FIG. 3A shows perspective view (with corresponding end view of FIG. 3B) of a medical device 300 having a greater expandability along a second radial direction 308 than along a first radial direction 306. When deployed, as shown in FIG. 3C (with corresponding end view of FIG. 3D), for example by self-expansion or balloon expansion, the frame 302 of the medical device 300 can expand from a compressed configuration 310 having a circular cross-section 315 to an expanded configuration 320 having an elliptical cross-section 325, for example within a body vessel. During expansion from the compressed configuration shown in FIGS. 3A-3B to the expanded configuration shown in FIGS. 3C-3D, the frame 302 provides a uniform expansion force directed radially outward from a longitudinal axis 304 in all directions. Four selected components of the radial expansion force are shown. Each of the force components is equal in magnitude, but different in direction. A first component 330 and a third component 334 of the radial expansion force are oppositely directed along a first radial direction 306. Similarly, a second component 332 and a fourth component 336 of the radial expansion force are oppositely directed along a second radial direction 308. In this embodiment, the radial expandability of the medical device 300 is less in the first radial direction 306 than in the second radial direction 308 because the frame 302 underwent greater radial expansion in the second radial direction 308 than in the first radial direction 306 in response to a uniform outward force in all directions.

In a fourth embodiment, a frame can, during expansion, exert a first radial expansion force along a first radial direction and a second, lesser, expansion force along a second radial direction. FIG. 4A shows a perspective view of a compressed delivery configuration 354 of a second expandable medical device 352 with an elliptical cross section, as shown in a corresponding end view in FIG. 4B. FIG. 4G shows the expanded configuration 356 of the medical device 352, with a circular cross section shown in end view of FIG. 4H. FIGS. 4C and 4D are all end views of the medical device of FIG. 4G showing the radial compressibility of the medical device to a force along a first direction or a second direction. FIGS. 4E and 4F are end views of the medical device of FIG. 4G showing the radial compressibility of the medical device to a force along a second direction.

Referring to FIGS. 4A and 4B, the medical device 352 in a compressed configuration 354 exerting a greater force along a first radial direction 306 than a second radial direction 308. When expanded from a compressed configuration 354, for example by self-expansion, the frame of the medical device 352 can expand from a compressed configuration 354 having an elliptical cross-section 355 to an expanded configuration 356 having a circular end view 360, for example within a body vessel. During expansion, this embodiment provides a non-uniform expansion force in different radial directions. Four selected components of the radial expansion force are shown in end view of FIGS. 4C and 4E during expansion. A first force 380 and a third force 384 are oppositely directed along a first radial direction 306 (FIG. 4C). Similarly, a second force 382 and a fourth force 386 are oppositely directed along a second radial direction 308 (FIG. 4E). As shown in FIG. 4D, the frame 352 expands along the first radial direction 306 with a first displacement 362. As shown in FIG. 4F, the frame 352 expands along the second radial direction 308 with a second displacement 366, which is less than the first displacement 362, as illustrated in a second schematic 392. Referring to FIGS. 4G and 4H, the frame in the expanded configuration 356 has a circular cross-section 365 after the expansion of the frame. Referring to FIGS. 4C-4F, when expansion of the medical device 352 occurs within a body vessel, movement of the frame 364 through the first displacement 362 can exert a greater force on the interior wall of the body vessel in the first radial direction 306 than along the second radial direction 308.

In one embodiment, the frame can have barbs for engaging a vessel wall positioned along a first radial direction 306. This frame can be expanded to a circular shape within an elliptical vessel, thereby temporarily distorting the vessel shape while the barbs engage the vessel wall. The frame can subsequently be compressed by the tension of the vessel wall into an elliptical expanded configuration. Thereafter, the frame can move between the elliptical and circular cross-sectional shapes in response to corresponding changes by the adjacent portions of a vessel wall.

In another embodiment, a self-expanding frame can be partially restrained by the interior wall of a body vessel, and provide a continuous force along a first radial direction 306 against a vessel wall so as to secure the frame within the vessel by maintaining a force against the vessel wall. The force can be calibrated to secure the frame in the vessel without substantially distorting the vessel. Preferably, after implantation deployment of a medical device of this embodiment within a target body vessel, the medical device will not substantially distort or enlarge the diameter of the interior of the body vessel. While the deployment of the medical device may temporarily enlarge the vessel wall to a greater extent, for example to securely attach the medical device to the interior of the body vessel, the medical device can thereafter assume a low profile configuration within the body vessel after deployment, preferably without a substantial or sustained distortion of the body vessel's interior diameter. For example, in one embodiment, after deployment, a medical device will remain in a body vessel without enlarging an interior distance across a body vessel by more than 50%, more preferably not more than about 25%, most preferably not more than 10%, compared to the comparable distance without the medical device present. In one embodiment, the ability of the frame to conform to fluctuations in the geometry of the body vessel interior permits the frame to minimally distort the interior distance across the body vessel. In some embodiments, the force against the vessel wall in the first radial direction 306 can be greater than the force against the vessel wall in the second radial direction 308.

Preferably, the frame can have compressed and expanded configurations. In some embodiments, the expanded configurations can be resiliently further extended in one or more radial directions. The expanded configuration or the compressed configuration may, in some embodiments, have a first maximum radial distance that is greater than a second maximum radial distance. For instance, in one embodiment, the frame has an elliptical cross-section. In other embodiments, the compressed or radial configuration can have a circular cross-section. Some embodiments have both circular and elliptical cross-sections at different parts of the medical device. Although the shape and configuration of the frame can comprise a substantially tubular structure, or a circular or elliptical cross-section, the frame does not have to possess these characteristics.

FIG. 5A is a perspective view of a medical device in a compressed delivery configuration with a circular cross section. FIG. 5B is a perspective view of a medical device in an expanded configuration having a hexagonal cross section, and optionally characterized by differing expandability or compressibility along different directions, as illustrated in the end views of FIGS. 5C, 5D, 5E and 5F, all of which correspond to the expanded frame of FIG. 5B. FIG. 5G is a perspective view of a medical device in an expanded configuration having an oval cross section, as shown in the corresponding end view of FIG. 5H. FIG. 5I is a perspective view of a medical device in an expanded configuration having a circular cross section, as shown in the corresponding end view of FIG. 5J. FIG. 5K is a perspective view of a medical device in an expanded configuration having an triangular cross section, as shown in the corresponding end view of FIG. 5L.

Referring to FIG. 5A, the frame can have a compressed configuration 400 having a longitudinal axis 402. The compressed configuration can expand into a variety of expanded configurations.

For example, in FIG. 5B, a frame 421 in a first expanded configuration 420 can have a hexagonal cross-section. In one embodiment, the hexagonal cross-section can be characterized by a different compressibility or expandability along a first radial direction 406, a second radial direction 408 or a third radial direction 409. For instance, as shown in FIG. 5C, a first unextended cross-section 422 (a cross-section of the expanded configuration 420 that is not extended) can be extended along the first radial direction 406 with a first expandability to form a first extended cross-section 426. The first expandability can be different than a second expandability for extension of the frame 421 along a second radial direction 408. Alternatively, as shown in FIG. 5D, the first extended cross-section 426 can be compressed along the first radial direction 406 with a first compressibility to form the first unextended cross-section 422. Furthermore, with reference to FIG. 5E, the first unextended cross-section 422 can be extended along the third radial direction 409 with a second expandability to form a second extended cross-section 428. The second expandability can be different than or the same as the first expandability. Alternatively, as shown in FIG. 5F, the second extended cross-section 428 can be compressed along the third radial direction 409 with a second compressibility to form the first unextended configuration 422. The third compressibility can be different than the first compressibility. The expandability in each direction can be the same or different from each other, or the same or different from the compressibility in any given direction.

Referring to FIGS. 5G and 5H, other embodiments provide a frame 431 forming a second expanded configuration 430 (FIG. 5G) having an elliptical cross-section 432 (FIG. 5H). In one embodiment, the elliptical cross-section has a particular compressibility or expandability along a first radial direction 406 and a second radial direction 408. Referring to FIGS. 5I and 5J, another embodiment has a frame 441 forming a third expanded configuration 440 (FIG. 5I) having a circular cross-section 442 (FIG. 5J), and having a particular compressibility or expandability along a first radial direction 406 and a second radial direction 408. Referring to FIGS. 5K and 5L, another embodiment provides a frame 451 forming a fourth expanded configuration 450 (FIG. 5K) having an triangular cross-section 452 (FIG. 5L), having a particular compressibility or expandability along a first radial direction 406 and a second radial direction 409. Although illustrated with tubular frame configurations for simplicity, the invention provides other embodiments having other configurations, including configurations with multiple different cross-sections along the longitudinal axis.

Preferably, a frame has a tubular configuration defining a lumen. In some embodiments, the frame is moveable between a compressed configuration (optionally defining a first lumen with a circular or elliptical cross section), and an expanded configuration (optionally defining a second lumen with a circular or an elliptical cross section). Preferably, the volume of the second lumen (the expanded configuration) is greater than the volume of the first lumen (the compressed configuration). The compressed configuration is preferably adapted for implantation within a body vessel, for instance from the distal portion of a delivery catheter. In one embodiment, the compressed configuration is crimped on a balloon on a delivery catheter. In another embodiment, the frame is self-expanding and the frame in the compressed configuration is retained by an outer sheath at the distal end of a catheter delivery system.

Frames with various compressibility or expandability characteristics can be designed in a variety of configurations. For example, the structure, thickness, density, material or permeability of the structure can be varied to impart particular properties of compressibility or expandability.

The frame can, in one embodiment, comprise a plurality of struts. Struts are structures that can resist longitudinal compression. Struts can be an identifiable segment of an elongated frame member, for example separated by bends in the member, individual segments joined together, or any combination thereof. Struts can have any suitable structure or orientation to allow the frame to provide a particular compressibility, expandability, or any combination thereof. For example, struts can be oriented substantially parallel to, substantially perpendicular to, or diagonal to the longitudinal axis of a tubular frame, or some combination thereof. Struts can be straight or arcuate in shape, and can be joined by any suitable method, or can form one or more distinct rings. In one embodiment, the frame comprises a plurality of struts connected by alternating bends. For example, in one embodiment, the frame can be an annular ring member comprising a series of struts in a "zig-zag" pattern. In some embodiments, the struts are substantially aligned along the surface of a tubular plane, substantially parallel to the longitudinal axis of the support frame.

The frame can, in some embodiments, have a non-uniform density of struts. For example, the frame can comprise a first circumferential region having continuously joined regions of a first and a second strut density per unit of circumferential distance which intersect the first and second radial directions, respectively. In one embodiment, the first strut density is greater than the second strut density.

Figure 6C:
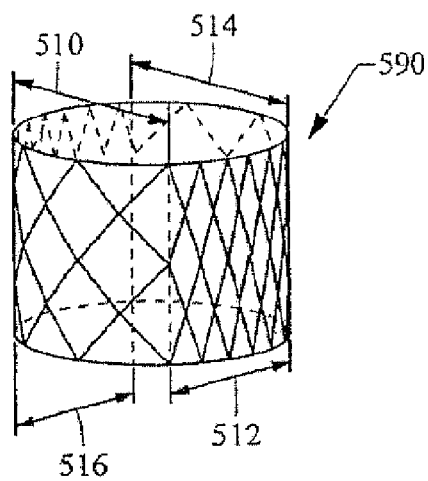
FIG. 6A is a diagram of an expandable medical device frame having various strut configurations and strut densities.

FIG. 6A is a diagram of an expandable medical device frame having various strut configurations and strut densities. FIG. 6B shows an end view of the medical device frame of FIG. 6A in a circular tubular configuration that is moveable to a second elliptical tubular configuration shown in the end view of FIG. 6C. Referring to FIG. 6A, a first frame 500 comprises a series of struts joined by bends in a "zig-zag" pattern. For example, the first frame 500 comprises a continuous bent frame member 502 formed in part by a first strut 506 joined to a second strut 504 by a first bend 505. The first frame 500 also comprises a first region 510 having a first strut density and continuously joined to a second region 512 having a second strut density that is greater than the first strut density. The second region 512 is continuously joined to a third region 514 having the same strut density as the first region 510. Finally, a fourth region 516 is continuously joined to the third region 514. In FIG. 6B, the first frame 500 can be folded into a first closed ring 580 having a circular cross-section. In FIG. 6C, the first closed ring 580 is moveable to a second closed ring 590 having an elliptical cross-section. For instance, first frame 500 can have greater expandability along a first radial direction than along a second radial direction, or a greater compressibility along a first radial direction than along a second radial direction.

Figure 7:
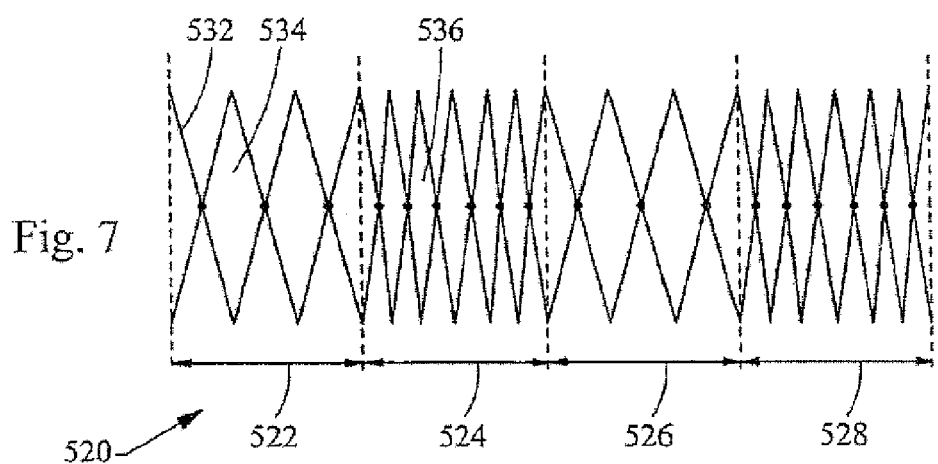
FIG. 7 is a diagram of an expandable medical device frame having various strut configurations and strut densities.

In another embodiment, shown in FIG. 7, the frame can be made of arrays of alternating "zig-zag" struts that are joined at one end or overlapping. For example, a second frame 520 comprises two arrays of struts as illustrated in the first frame 500 that are joined at one end to form repeating arrays of different shapes of diamond-shaped cells. The first region 522 and the third region 526 comprise repeating first diamond-shaped cells 534, while the second region 524 and the fourth region 528 comprise repeating second diamond-shaped cells 536 that are smaller than the first-shaped cells.

Figure 8:
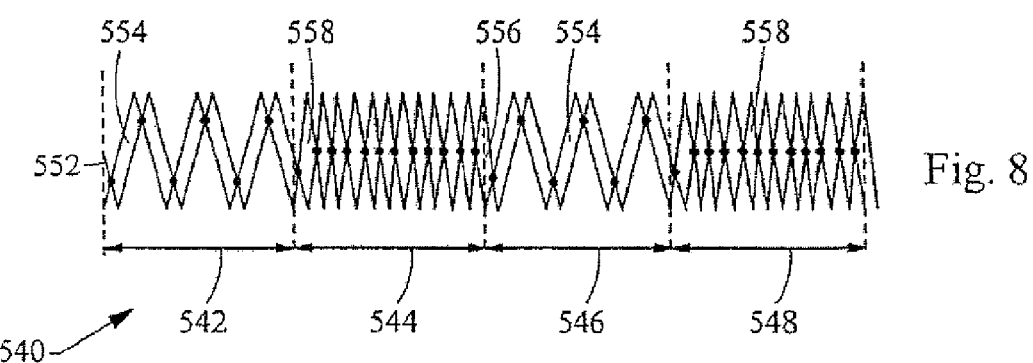
FIG. 8 is a diagram of an expandable medical device frame having various strut configurations and strut densities.

Referring to FIG. 8, another embodiment provides a third frame 540 comprises two arrays of struts as illustrated in the first frame 500 that are joined in an overlapping fashion to form repeating arrays of differently shaped cells. The first region 542 and the third region 546 comprise repeating first cells 554, while the second region 544 and the fourth region 548 comprise repeating second, diamond-shaped, cells 558 that have a different shape than the first cells 554. Third cells 556, which can have different shapes than the first cells 554 and the second cells 558, are also present at the juncture between regions. Like the first frame 500, these other frames can be rolled into annular forms, for example by joining the first region 522 of the second frame 520 to its fourth region 528, or by joining the first region 542 of the third frame 540 to its fourth region 548. Multiple annular frame forms can also be joined and stacked, in some embodiments, to form more elongated tubular frames.

In some embodiments, the cross-sectional area of struts can be varied to provide a frame with a particular direction-specific compressibility or expandability. For example, a frame can comprise struts with different cross-sectional areas, or have a cross-sectional area that varies along the length, width or height of any individual strut. In some embodiments, directional dependence of compressibility or expandability can be imparted to a frame by changing the cross-sectional area of the frame in selected areas. For example, a frame having some struts with a larger cross-sectional area than others can decrease the compressibility of the frame in a first direction compared with the compressibility of the frame in a second direction.

FIG. 9A is a diagram of an expandable medical device frame having struts with different cross-sectional areas. A frame member 602 in a flat plane configuration 600 comprises a frame member 602 formed from a plurality of alternating struts joined by bends in a "zig-zag" pattern. Preferably, one or more frame members 602 can be formed as a tubular configuration 680, as shown in FIG. 9D. For example, the pattern of the frame member 602 can be laser cut from a tube of a suitable material, such as a self-expanding NiTi alloy, in the tubular configuration 680, or the ends of the frame member 602 can joined to form the tubular configuration 680. The frame member 602 includes a first region 610 joined to a second region 612. FIG. 9B shows a cross sectional view of the struts of the frame member 602 in the first region 610, which have a first width 604 and a first height 605 throughout each strut, providing a first cross-sectional area 606. FIG. 9C shows a cross sectional view of the struts of the frame member 602 in the second region 612 have a second width 608 and a second height 607 throughout each strut, providing a second cross-sectional area 609. In this embodiment, the first height 605 is greater than the second height 607, while the first width 604 and the second width 608 are substantially equal. Therefore, the first cross-sectional area 606 (FIG. 9B) is greater than the second cross-sectional area 609 (FIG. 9C).

Optionally, the frame member 602 further comprises repeating regions having struts of differing cross sections. In FIG. 9A, the second region 612 can be continuously joined to a third region 614, comprising struts with a first cross-sectional area 606 like the struts of the first region 610. Similarly, the third region 614 can be continuously joined to a fourth region 616, comprising struts with a second cross-sectional area 609 like the struts of the second region 612.

Optionally, multiple frame members 602 can be joined end to end or in an overlapping fashion. In FIG. 10, for example, a frame 620 is formed by stacking multiple frame members from FIG. 9A end to end to form an array of repeating diamond-shape cells with the same dimensions and strut thicknesses as frame member 602 in FIG. 9A. The first region 622 and the third region 626 comprise first cells 632 completely enclosed by struts having a first cross-sectional area 606. The second region 624 and the fourth region 628 comprise second cells 636 completely enclosed by struts having a second cross-sectional area 609, that is smaller than the first cross-sectional area 606. Areas between the regions have transition cells 634 formed by some struts with the first cross-sectional area 606 and other struts with the second cross-sectional area 609.

In another embodiment, the frame struts can have non-uniform cross-sectional areas. For example, though not illustrated in FIG. 9A-9D or in FIG. 10, individual struts can have varying cross-sectional areas along their length, width or height. For instance, portions of a strut can have a first cross-sectional area that is less than a second cross-sectional area of another portion of the same strut or a portion of a different strut.

In another embodiment, the frame struts can have various capacities to absorb fluid, thereby imparting variable compressibility or expandability characteristics to the frame when exposed to fluid, such as body fluid in a body vessel.

Suitable support frames can also have a variety of configurations, including braided strands, helically wound strands, ring members, consecutively attached ring members, tube members, and frames cut from solid tubes. Also, suitable frames can have a variety of sizes. The exact configuration and size chosen will depend on several factors, including the desired delivery technique, the nature of the vessel in which the device will be implanted, and the size of the vessel. A frame structure and configuration can be chosen to facilitate maintenance of the device in the vessel following implantation.

The support frame can be made from one or more suitable materials. Examples of suitable materials include, without limitation: stainless steel (such as 316 stainless steel), nickel titanium (NiTi) alloys (such as Nitinol) and other shape memory and/or superelastic materials, MP35N, gold, silver, a cobalt-chromium alloy, tantalum, platinum or platinum iridium, or other biocompatible metals and/or alloys such as carbon or carbon fiber, cellulose acetate, cellulose nitrate, silicone, cross-linked polyvinyl alcohol (PVA) hydrogel, cross-linked PVA hydrogel foam, polyurethane, polyamide, styrene isobutylene-styrene block copolymer (Kraton), polyethylene teraphthalate, polyurethane, polyamide, polyester, polyorthoester, polyanhidride, polyether sulfone, polycarbonate, polypropylene, high molecular weight polyethylene, polytetrafluoroethylene, or other biocompatible polymeric material, or mixture of copolymers thereof, or stainless steel, polymers, and any suitable composite material.

In one embodiment, the frame is self-expanding. Upon compression, self-expanding frames can expand toward their pre-compression geometry. In some embodiments, a self-expanding frame can be compressed into a low-profile delivery conformation and then constrained within a delivery system for delivery to a point of treatment in the lumen of a body vessel. At the point of treatment, the self-expanding frame can be released and allowed to subsequently expand to another configuration. In certain embodiments, the frame is formed partially or completely of alloys such as nitinol (NiTi) which have superelastic (SE) characteristics. However, while some embodiments provide frames made from shape memory materials, other embodiments comprise other materials such as stainless steel, MP35N and other suitable materials. Some embodiments provide frames that are not self-expanding, or that do not comprise superelastic materials.

The support frame can be formed in any suitable shape, including a ring, a stent, a tube, or a zig-zag configuration. In one embodiment, the support frame can be self-expanding or balloon-expandable.

The support frame can be formed from a variety of medical grade polymers having properties that permit the frame to function as a supporting structure for the remodelable material. In some embodiments, the support frame comprises a bioabsorbable or remodelable material.

The support frame can comprise a bioabsorbable material that can be degraded and absorbed by the body over time to advantageously eliminate a frame structure from the vessel before, during or after the remodeling process. A number of bioabsorbable homopolymers, copolymers, or blends of bioabsorbable polymers are known in the medical arts. These include, but are not necessarily limited to, polyesters, poly (amino acids), copoly(ether-esters), polyalkylenes oxalates, polyamides, poly(iminocarbonates), polyorthoesters, polyoxaesters, polyamidoesters, polyoxaesters containing amido groups, poly(anhydrides), polyphosphazenes, poly-alpha-hydroxy acids, trimethlyene carbonate, poly-beta-hydroxy acids, polyorganophosphazines, polyanhydrides, polyesteramides, polyethylene oxide, polyester-ethers, polyphosphoester, polyphosphoester urethane, cyanoacrylates, poly(trimethylene carbonate), poly(iminocarbonate), polyalkylene oxalates, polyvinylpyrolidone, polyvinyl alcohol, poly-N-(2-hydroxypropyl)-methacrylamide, polyglycols, aliphatic polyesters, poly(orthoesters), poly(ester-amides), polyanhydrides, modified polysaccharides and modified proteins.

Some specific examples of bioabsorbable materials include polymers and co-polymers comprising a polylactic acid, a polyglycolic acid, a polycaprolactone or derivatives thereof. Suitable bioabsorbable materials for a frame include: poly(epsilon-caprolactone), poly(dimethyl glycolic acid), poly(hydroxy butyrate), poly(p-dioxanone), polydioxanone, PEO/PLA, PLA, poly(lactide-co-glycolide), poly(hydroxy-butyrate-co-valerate), poly(glycolic acid-co-trimethylene carbonate), poly(epsilon-caprolactone-co-p-dioxanone), poly-L-glutamic acid or poly-L-lysine, polylactic acid, polylactide, polyglycolic acid, polyglycolide, poly(D,L-lactic acid), L-polylactic acid, poly(glycolic acid), polyhydroxyvalerate, cellulose, chitin, dextran, fibrin, casein, fibrinogen, starch, collagen, hyaluronic acid, hydroxyethyl starch, and gelatin. A frame may also comprise one or more naturally derived bioabsorbable polymers, including modified polysaccharides such as cellulose, chitin, and dextran or modified proteins such as fibrin and casein.

The frame can include structural features, such as barbs, that maintain the frame in position following implantation in a body vessel. The art provides a wide variety of structural features that are acceptable for use in the medical device, and any suitable structural feature can be used. Furthermore, barbs can also comprise separate members attached to the frame by suitable attachment means, such as welding and bonding. For instance, barbs can be formed by V-shaped cuts transversing the thickness of a flat metal frame, which are bent outward to form the barb. In some embodiments, the number, arrangement, and configuration of the integral barbs can vary according to design preference and the clinical use of the device. The barbs can have any suitable shape, including points or "fish hook"-like configurations. The barbs may or may not penetrate the vein wall, depending on their design and other factors, including the thickness and type of covering used.

Also provided are embodiments wherein the frame comprises a means for orienting the frame within a body lumen. For example, the frame can comprise a marker, such as a radiopaque portion of the frame that would be seen by remote imaging methods including X-ray, ultrasound, Magnetic Resonance Imaging and the like, or by detecting a signal from or corresponding to the marker. In other embodiments, the delivery device can comprise a frame with indicia relating to the orientation of the frame within the body vessel. In other embodiments, indicia can be located, for example, on a portion of a delivery catheter that can be correlated to the location of the frame within a body vessel.

A frame or delivery device may comprise one or more radiopaque materials to facilitate tracking and positioning of the medical device, which may be added in any fabrication method or absorbed into or sprayed onto the surface of part or all of the medical device. The degree of radiopacity contrast can be altered by implant content. Radiopacity may be imparted by covalently binding iodine to the polymer monomeric building blocks of the elements of the implant. Common radiopaque materials include barium sulfate, bismuth subcarbonate, and zirconium dioxide. Other radiopaque elements include: cadmium, tungsten, gold, tantalum, bismuth, platium, iridium, and rhodium. In one preferred embodiment, iodine may be employed for its radiopacity and antimicrobial properties. Radiopacity is typically determined by fluoroscope or x-ray film. Various other ways to incorporate radiopaque material in a medical device are provided in copending application Ser. No. 10/787,307, filed Feb. 26, 2004 by Case et al., entitled "Prosthesis Adapted for Placement Under External Imaging," which is incorporated herein by reference. Imagable markers, including radiopaque material, can be incorporated in any portion of a medical device. For example, radiopaque markers can be used to identify a long axis or a short axis of a medical device within a body vessel. For instance, radiopaque material may be attached to a frame or woven into portions of the valve member material.

The invention also relates to embodiments comprising a frame and a means for regulating fluid through a body vessel. In some embodiments, the fluid can flow through the frame, while other embodiments provide for fluid flow through a lumen defined by the frame. Some embodiments comprise a frame and a first valve member connected to the frame. In one embodiment, the valve member is a flexible leaflet attached to the frame along at least one edge and extending into the lumen of the body vessel. A valve member, according to some embodiments, can comprise a valve member, such as a free edge of a leaflet, that is responsive to the flow of fluid through the body vessel. One or more valve members attached to a frame may, in one embodiment, permit fluid to flow through a body vessel in a first direction while substantially preventing fluid flow in the opposite direction. In some embodiments, the valve member comprises an extracellular matrix material, such as small intestine submucosa (SIS).

In one preferred embodiment, medical devices comprising a frame and a valve member can be used to regulate fluid flow in a vein, for example to treat venous valve incompetency. For example, one or more medical devices comprising a frame and one or more valve members can be implanted in a vein with incompetent venous valves so as to provide a valve to replace the incompetent valves therein.

A wide variety of materials acceptable for use as the valve members are known in the art, and any suitable material can be utilized. The material chosen need only be able to perform as described herein, and be biocompatible, or able to be made biocompatible. Examples of suitable materials include flexible materials, natural materials, and synthetic materials. Examples of suitable natural materials include collagen and extracellular matrix (ECM) material, such as submucosa. Small intestine submucosa (SIS) is particularly well-suited for use as valve members, such as leaflets. Examples of suitable synthetic materials include polymeric materials, such as polypropylene, polyurethane, expanded polytetrafluoroethylene (ePTFE), polyurethane (PU), polyethylene terphthalate (PET), silicone, latex, polyethylene, polypropylene, polycarbonate, nylon, polytetrafluoroethylene, polyimide, polyester, and mixture thereof, or other suitable materials.

The valve members can be attached to the frame with any suitable attachment mechanism, such as sutures, adhesives, bonding, and the like. The attachment mechanism chosen will depend on the nature of the frame and valve members. Sutures provide an acceptable attachment mechanism when SIS or other ECM materials are used as the valve members with a metal or plastic frame.

The device can include any suitable number of valve members. The valve members need only be able to provide the functionality described herein. The specific number chosen will depend on several factors, including the type and configuration of the frame.

Figure 11A:
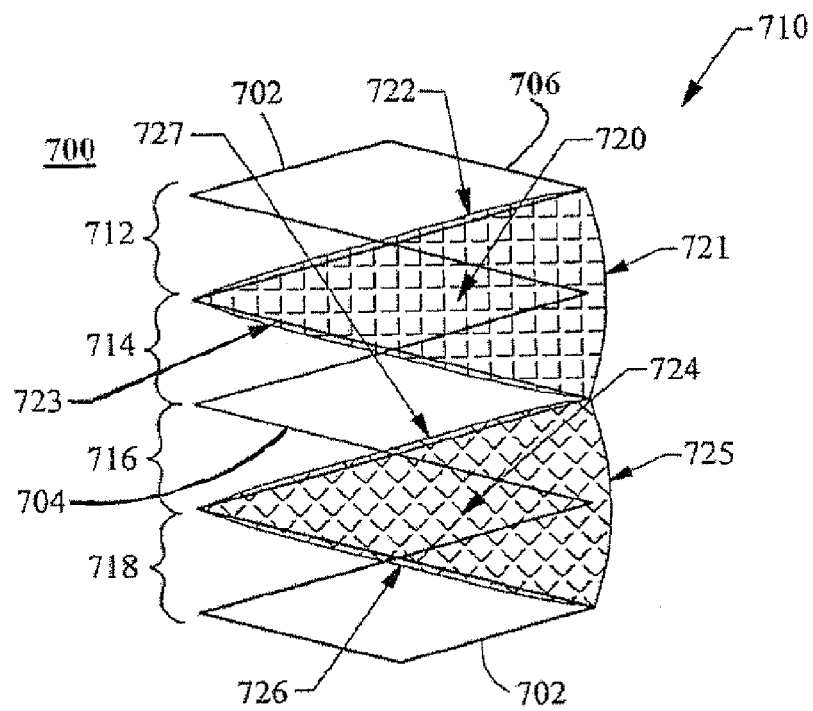
FIG. 11A is a diagram of a medical device comprising a frame and two valve members, according to some embodiments of the invention.
Figure 11B:
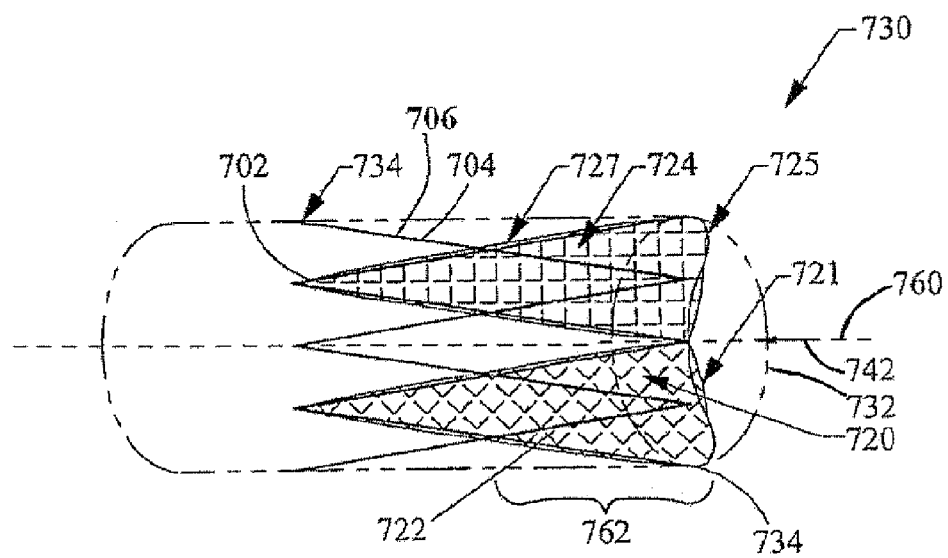
FIG. 11B shows the device of FIG. 11B in a tubular configuration, having end views shown in FIG. 11C or FIG. 11D, depending on the position of the valve.
Figure 11C:
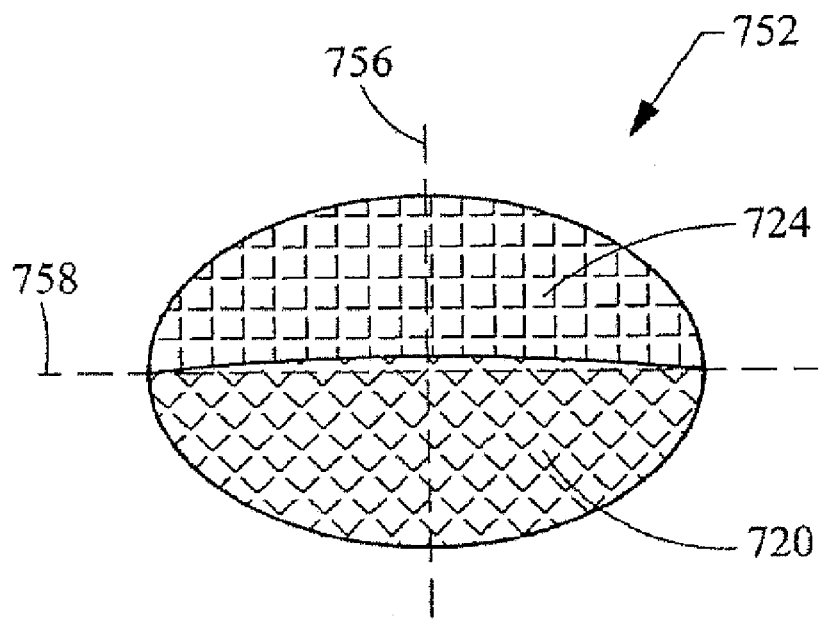
Figure 11D:
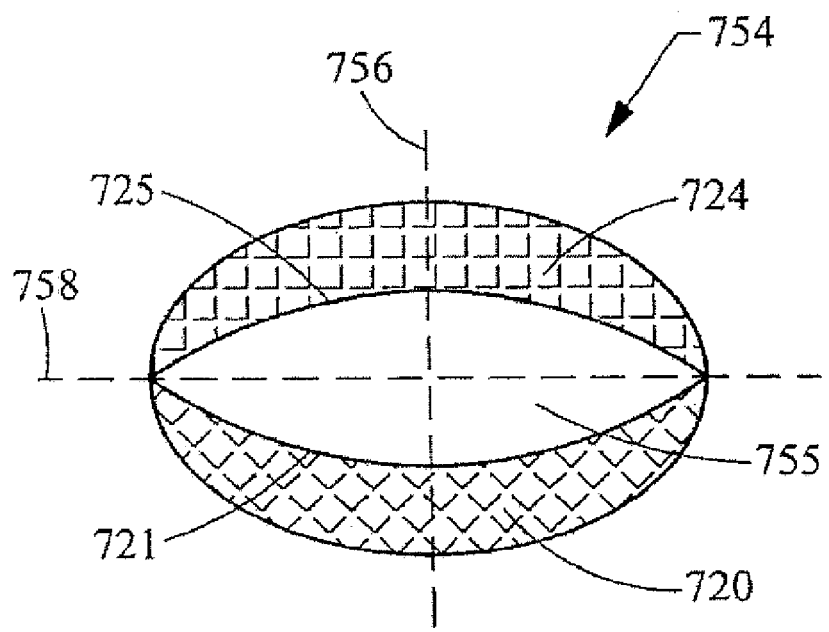

FIGS. 11A-11D show a medical device 700 of one embodiment comprising a frame 704 and two valve members. FIG. 11A shows a medical device in a flat plan configuration 710; FIG. 11B shows the same medical device in a tubular configuration 730. FIG. 11C shows an end view of the medical device in the closed valve configuration 752; FIG. 11D shows an end view of the medical device in the open valve configuration 754.

The frame 704 comprises two "zig-zag" frame members joined to form a linear chain of diamond-shaped cells. The frame 704 comprises four regions. The first region 712 and the third region 716 comprise thick struts 702 having a first cross-section. The second region 714 and the fourth region 718 comprise thin struts 706 having a second cross-section that is less than the first cross-section.

The medical device comprises two valve members that are a first leaflet 720 and a second leaflet 724. Each leaflet has three sides and is attached to the frame 704 along two sides of the leaflet. The first leaflet 720 is attached to the frame along a first edge 722 and along a second edge 723 by suturing the leaflet around the frame. The remaining third edge 721 is a free edge that is flexible enough to move in response to fluid flowing past the leaflet. Similarly, the second leaflet 724 is attached to the frame along a first edge 726 and along a second edge 727 by suturing the leaflet around the frame. The remaining third edge 725 is a free edge that is flexible enough to move in response to fluid flowing past the leaflet.

In FIG. 11B, the frame 704 is in a tubular configuration 730. The tubular configuration 730 can be formed in any suitable manner. In one aspect, the tubular configuration 730 is formed by joining the fourth region 718 of the frame 704 to the first region 712 of the planar configuration 710. In another aspect, the tubular configuration 730 is formed by laser-cutting holes in a cylinder of material, such as a self-expanding NiTi alloy, to form the medical device frame 704 in the tubular configuration 730. The frame 704 in the tubular configuration 730 is expandable between a low profile compressed configuration having a circular cross-section and the expanded configuration with an elliptical cross-section 750. When expanded, the tubular configuration 730 has a greater radial compressibility along a second radial direction 758 than along a first radial direction 756, where the first and second radial directions are perpendicular to each other and to the longitudinal axis 760 of the tubular configuration 730. In this embodiment, the directional dependence on compressibility of the frame 704 in its tubular configuration 730 results from the presence and arrangement of the thick struts 702 and the thin struts 706, as well as the properties of the frame material itself.

The tubular configuration 730 is deployed with its longitudinal axis 760 substantially parallel to that of the lumen of a body vessel 732. The tubular configuration 730 includes a passageway that allows fluid flow in a first direction 740, while substantially reducing or preventing fluid flow in the opposite direction 742, by action of the leaflets in response to fluid flow within the body vessel. In the tubular configuration 730, the first leaflet 720 and the second leaflet 724 are disposed opposite each other, so as to form a coaptation region 762 where the two leaflets can cooperate to regulate fluid flow through a body vessel 732. The coaptation region 762 is a length along which the valve members contact each other when the valve members are in a closed configuration. In this case, the free edge of first leaflet 720 and the free edge of the second leaflet 724 can contact each other to regulate fluid flow through the frame. More specifically, as shown in the end view of FIG. 11D, the free edges of one or more leaflets can be pushed into an open configuration 754 in response to fluid flow in a first direction 740 through a body vessel 732. As shown in the end view of FIG. 11C, the free edges of one or more leaflets can move to a closed configuration 752 to substantially prevent retrograde fluid flow in a second direction 742, opposite the first direction 740. One or more valve members can define a valve orifice through which fluid in the body vessel can pass. In the embodiment illustrated in FIG. 7, the free edges of each leaflet can open to form a valve orifice 755 through which fluid can flow in a first direction 740. In some embodiments, the frame 704 can comprise one or more barbs 734 that can secure the tubular configuration 730 within the body vessel 732. In some embodiments, a first and a second valve member each attached to a frame and each comprising a leaflet free edge moveable in response to fluid flow, can cooperably define a valve orifice through with fluid can flow.

Preferably, the medical device is implanted in a compressed tubular configuration, and expanded at a point of treatment within a body vessel. The overall configuration, cross-sectional area, and length of the frame 704 in the tubular configuration 730 (compressed or expanded) will depend on several factors, including the size and configuration of device, the size and configuration of the vessel in which the device will be implanted, the extent of contact between the device and the walls of the vessel, and the amount of retrograde flow through the vessel that is desired.

Although the medical device 700 is shown with two valve members, other embodiments provide medical devices comprising 1, 3, 4, 5, 6, 7, 8 or more valve members. The valve members can be arranged in any suitable configuration with respect to one another and the frame. In one preferred embodiment, a medical device can comprise a frame and three valve members that are leaflets comprising free edges. In another preferred embodiment, a medical device can comprise one leaflet having a free edge that can sealably engage the interior of a vessel wall. Other suitable configurations of valve members are provided by further embodiments, including differently shaped valve members, and different points of attachment by valve members to the frame.

In one embodiment, the valve members are substantially oriented parallel to the longitudinal axis of a medical device. The orientation of a valve member in a medical device is discussed in copending application Ser. No. 10/787,307, filed Feb. 26, 2004 by Case et al., entitled "Prosthesis Adapted for Placement Under External Imaging," which is incorporated herein by reference.

In devices including multiple openings that permit a controlled amount of fluid flow in the second, opposite direction to flow through the vessel in which the device is implanted, the total open area of all openings can be optimized as described above, but it is not necessary that the individual openings have equivalent total open areas.

The invention also provides methods of making medical devices for implantation in a body vessel. In one embodiment, the method comprises the step of attaching a first valve member to a frame. The valve member can be responsive to the flow of fluid through the frame, and adapted to permit fluid flow through said vessel in a first direction or substantially prevent fluid flow through said vessel in a second, opposite direction. The frame can have a longitudinal axis, a first radial compressibility along a first radial direction that is less than a second radial compressibility along a second radial direction.

In some embodiments, the medical devices can be configured for delivery to a body vessel. For example, a medical device can be compressed to a delivery configuration within a retaining sheath that is part of a delivery system, such as a catheter-based system. Upon delivery, the delivery configuration can be expanded, for example, by removing a self-expanding frame, or portion thereof, from the sheath or by inflating a balloon from inside the medical device. The delivery configuration can be maintained prior to deployment of the medical device by any suitable means, including a sheath, a suture, a tube or other restraining material around all or part of the compressed medical device, or other methods.

In some embodiments, a bioabsorbable suture or sheath can be used to maintain a medical device in a compressed configuration both prior to and after deployment. As the bioabsorbable sheath or suture is degraded by the body after deployment, the medical device can expand within the body vessel. In some embodiments, a portion of the medical device can be restrained with a bioabsorbable material and another portion allowed to expand immediately upon implantation. For example, a self-expanding frame can be partially restrained by a bioabsorbable material upon deployment and later expand as the bioabsorbable material is absorbed.

Still other embodiments provide methods of treating a subject, which can be animal or human, comprising the step of providing one or more frames as described herein. Other methods further comprise the step of providing one or more frames attached to one or more valve members, as described herein. In some embodiments, methods of treating may also provide the step of delivering a medical device to a point of treatment in a body vessel, or deploying a medical device at the point of treatment, wherein the medical devices are as described herein.

The invention also provides methods of treating a patient. In one embodiment the method comprises a step of delivering a medical device as described herein to a point of treatment in a body vessel, and deploying the medical device at the point of treatment. The delivering step can comprise delivery by surgical or by percutaneous delivery techniques known to those skilled in the art.

Methods for treating certain conditions are also provided, such as venous valve insufficiency, varicose veins, esophageal reflux, restinosis or atherosclerosis. In some embodiments, the invention relates to methods of treating venous valve related conditions.

A "venous valve related condition" is any condition presenting symptoms that can be diagnostically associated with improper function of one or more venous valves. In mammalian veins, natural valves are positioned along the length of the vessel in the form of leaflets disposed annularly along the inside wall of the vein which open to permit blood flow toward the heart and close to prevent back flow. These natural venous valves act as open to permit the flow of fluid in the desired direction, and close upon a change in pressure, such as a transition from systole to diastole. When blood flows through the vein, the pressure forces the valve leaflets apart as they flex in the direction of blood flow and move towards the inside wall of the vessel, creating an opening therebetween for blood flow. The leaflets, however, do not normally bend in the opposite direction and therefore return to a closed position to restrict or prevent blood flow in the opposite, i.e. retrograde, direction after the pressure is relieved. The leaflets, when functioning properly, extend radially inwardly toward one another such that the tips contact each other to block backflow of blood. Two examples of venous valve related conditions are chronic venous insufficiency and varicose veins.

In the condition of venous valve insufficiency, the valve leaflets do not function properly. For example, the vein can be too large in relation to the leaflets so that the leaflets cannot come into adequate contact to prevent backflow (primary venous valve insufficiency), or as a result of clotting within the vein that thickens the leaflets (secondary venous valve insufficiency). Incompetent venous valves can result in symptoms such as swelling and varicose veins, causing great discomfort and pain to the patient. If left untreated, venous valve insufficiency can result in excessive retrograde venous blood flow through incompetent venous valves, which can cause venous stasis ulcers of the skin and subcutaneous tissue. Venous valve insufficiency can occur, for example, in the superficial venous system, such as the saphenous veins in the leg, or in the deep venous system, such as the femoral and popliteal veins extending along the back of the knee to the groin.

The varicose vein condition consists of dilatation and tortuosity of the superficial veins of the lower limb and resulting cosmetic impairment, pain and ulceration. Primary varicose veins are the result of primary incompetence of the venous valves of the superficial venous system. Secondary varicose veins occur as the result of deep venous hypertension which has damaged the valves of the perforating veins, as well as the deep venous valves. The initial defect in primary varicose veins often involves localized incompetence of a venous valve thus allowing reflux of blood from the deep venous system to the superficial venous system. This incompetence is traditionally thought to arise at the saphenofemoral junction but may also start at the perforators. Thus, gross saphenofemoral valvular dysfunction may be present in even mild varicose veins with competent distal veins. Even in the presence of incompetent perforation, occlusion of the saphenofemoral junction usually normalizes venous pressure.

The initial defect in secondary varicose veins is often incompetence of a venous valve secondary to hypertension in the deep venous system. Since this increased pressure is manifested in the deep and perforating veins, correction of one site of incompetence could clearly be insufficient as other sites of incompetence will be prone to develop. However, repair of the deep vein valves would correct the deep venous hypertension and could potentially correct the secondary valve failure. Apart from the initial defect, the pathophysiology is similar to that of varicose veins.

Methods for delivering a medical device as described herein to any suitable body vessel are also provided, such as a vein, artery, billiary duct, ureteral vessel, body passage or portion of the alimentary canal.

The invention includes other embodiments within the scope of the claims, and variations of all embodiments.

We claim:

1. A method of treating a subject with a medical device for implantation in a body vessel of the venous system, said body vessel comprising an elliptical cross-section having a major axis and a minor axis wherein the cross-section of the body vessel can undergo change as a result of blood flowing therethrough, comprising the steps of:
   (a) radially compressing a medical device into a radially compressed delivery configuration, the medical device comprising
      (i) an elliptical annular frame having a tubular configuration defining a lumen about a longitudinal axis, the frame being movable between an expanded configuration and a compressed configuration, the frame in the expanded configuration having an elliptical cross-section having a major axis and a minor axis, where the frame has a first maximum radial distance along the major axis greater than a second maximum radial distance along the minor axis, the frame having a circular cross-section in the radially compressed delivery configuration, the frame including at least one annular ring member having at least two circumferential regions forming a closed ring frame, each circumferential region having a different radial compressibility, wherein the radial compressibility of the circumferential region along the major axis is greater than the radial compressibility along the minor axis, and
      (ii) one or two valve leaflets attached to the frame, the valve leaflet having a free edge unattached to the frame and positioned within the lumen of the frame along the major axis of the elliptical cross-section of the frame, the free edge of the one or more valve leaflets moveable in response to fluid flow through the lumen;
   (b) delivering the medical device in the radially compressed delivery configuration to a point of treatment within said body vessel of the venous system; and
   (c) deploying the medical device at the point of treatment by radially expanding the medical device from the radially compressed delivery configuration to a radially expanded configuration such that the major and minor axes of the frame are substantially aligned with the major and minor axes of said body vessel respectively, wherein the cross-section of the frame is configured to move between the elliptical cross-section and the circular cross-section to conform to the changing cross-section of said body vessel of the venous system.

2. The method of claim 1, wherein the frame includes a first annular ring member and a second annular ring member longitudinally adjacent to the first annular ring member, wherein the frame having an elliptical cross-section at the first annular ring member and a circular cross-section at the second annular ring member.

3. The method of claim 2, wherein the first and second annular ring members each have a first radial compressibility along a first radial direction perpendicular to the longitudinal axis that is greater than a second radial compressibility along a second radial direction perpendicular to the longitudinal axis and the first radial direction, the first and second radial compressibility of the second annular ring member being different than the first and second radial compressibility of the first annular ring member.

4. The method of claim 1, wherein the medical device further comprises a means for orienting the medical device within a body vessel.

5. The method of claim 1, wherein the at least one annular ring member of the frame comprises a plurality of interconnected linear struts and bends arranged in a zig-zag pattern extending circumferentially around the longitudinal axis to form the closed ring frame.

6. The method of claim 5, wherein each annular ring has a first circumferential region and a second circumferential region, the first circumferential region having a first strut density per unit of circumferential distance; and the second circumferential region having a second strut density per unit of circumferential distance, that is less than the first strut density.

7. The method of claim 5, wherein each annular ring has a first circumferential region and a second circumferential region, the first circumferential region having struts with a first strut cross-sectional area; and the second circumferential region having struts with a second strut cross-sectional area that is less than the first strut cross-sectional area.

8. The method of claim 1, where the frame comprises a material selected from the group consisting of: a stainless steel, a NiTi alloy and a cobalt-chromium alloy.

* * * * *